United States Patent
Behan et al.

(10) Patent No.: US 12,004,758 B2
(45) Date of Patent: *Jun. 11, 2024

(54) CATHETER FOR ACCESSING THE VASCULATURE INCLUDING THE NEUROVASCULATURE, AND METHODS OF USE

(71) Applicant: Julier Medical AG, Dubendorf (CH)

(72) Inventors: Niall Behan, Dubendorf (CH); Laurent Grandidier, Zollikerberg (CH)

(73) Assignee: Julier Medical AG, Dübendorf (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/455,426

(22) Filed: Aug. 24, 2023

(65) Prior Publication Data

US 2023/0397919 A1    Dec. 14, 2023

Related U.S. Application Data

(63) Continuation of application No. 18/156,585, filed on Jan. 19, 2023, now Pat. No. 11,737,767.
(Continued)

(51) Int. Cl.
*A61B 17/22*    (2006.01)

(52) U.S. Cl.
CPC .... *A61B 17/22* (2013.01); *A61B 2017/22038* (2013.01); *A61B 2017/22079* (2013.01)

(58) Field of Classification Search
CPC . A61B 17/22; A61B 17/221; A61B 17/00234; A61B 2017/22038; A61B 2017/22079
See application file for complete search history.

(56) References Cited

U.S. PATENT DOCUMENTS 3,868,956 A    3/1975  Alfidi et al.
3,946,741 A    3/1976  Adair
(Continued)

FOREIGN PATENT DOCUMENTS

DE    102011100733 A1    11/2012
EP         0379794 A1     8/1990
(Continued)

OTHER PUBLICATIONS

Alawieh, et al., Impact of Procedure Time on Outcomes of Thrombectomy for Stroke, JACC, 73(8):779-890 (Mar. 2019).
(Continued)

*Primary Examiner* — Tuan V Nguyen
(74) *Attorney, Agent, or Firm* — Eversheds Sutherland (US) LLP; Christopher C. Bolten; Albert K. Heng

(57) ABSTRACT

An improved catheter is provided for removing an obstruction(s) from a blood vessel, for example, for retrieving a clot/thrombus in the neurovasculature for the treatment of stroke. The catheter has a collapsed state sufficiently small and flexible for easier delivery through challenging vasculature and also has an expanded state sufficiently sized and robust for removing the obstruction. The catheter may include a self-collapsing and expanding mechanism to transition a portion of an outer tube (e.g., a braided portion) between the collapsed and expanded states. Such mechanism may include an inner actuator tube slidable over an actuation wire to collapse a distal branched section of the actuation wire, thereby collapsing the braided portion. The catheter may also include an intermediate coiled tube for reinforcing the braided portion in the expanded state.

30 Claims, 13 Drawing Sheets

Related U.S. Application Data

(60) Provisional application No. 63/267,032, filed on Jan. 21, 2022.

(56) References Cited

U.S. PATENT DOCUMENTS

| | | |
|---|---|---|
| 4,228,802 A | 10/1980 | Trott |
| 4,329,995 A | 5/1982 | Anthracite |
| 4,762,125 A | 8/1988 | Leiman et al. |
| 4,873,978 A | 10/1989 | Ginsburg |
| 4,926,858 A | 5/1990 | Gifford, III et al. |
| 5,011,488 A | 4/1991 | Ginsburg |
| 5,030,201 A | 7/1991 | Palestrant |
| 5,092,839 A | 3/1992 | Kipperman |
| 5,102,415 A | 4/1992 | Guenther et al. |
| 5,234,425 A | 8/1993 | Fogarty et al. |
| 5,256,146 A | 10/1993 | Ensminger et al. |
| 5,318,532 A | 6/1994 | Frassica |
| 5,458,573 A | 10/1995 | Summers |
| 5,695,499 A * | 12/1997 | Helgerson ............... A61F 2/95 606/198 |
| 5,776,096 A | 7/1998 | Fields |
| 5,807,311 A | 9/1998 | Palestrant |
| 5,827,243 A | 10/1998 | Palestrant |
| 5,893,869 A | 4/1999 | Barnhart et al. |
| 5,941,869 A | 8/1999 | Patterson et al. |
| 5,972,019 A | 10/1999 | Engelson et al. |
| 6,066,149 A | 5/2000 | Samson et al. |
| 6,159,195 A | 12/2000 | Ha et al. |
| 6,183,492 B1 | 2/2001 | Hart et al. |
| 6,206,868 B1 | 3/2001 | Parodi |
| 6,238,412 B1 | 5/2001 | Dubrul et al. |
| 6,280,464 B1 | 8/2001 | Hayashi |
| 6,319,242 B1 | 11/2001 | Patterson et al. |
| 6,350,271 B1 | 2/2002 | Kurz et al. |
| 6,454,790 B1 | 9/2002 | Neuberger et al. |
| 6,596,011 B2 | 7/2003 | Johnson et al. |
| 6,626,886 B1 | 9/2003 | Barbut |
| 6,632,236 B2 | 10/2003 | Hogendijk |
| 6,679,893 B1 | 1/2004 | Tran |
| 6,685,718 B1 | 2/2004 | Wyzgala et al. |
| 6,685,722 B1 | 2/2004 | Rosenbluth et al. |
| 6,692,504 B2 | 2/2004 | Kurz et al. |
| 6,699,260 B2 | 3/2004 | Dubrul et al. |
| 6,783,522 B2 | 8/2004 | Fischell |
| 6,824,545 B2 | 11/2004 | Sepetka et al. |
| 6,929,634 B2 | 8/2005 | Dorros et al. |
| 7,008,434 B2 | 3/2006 | Kurz et al. |
| 7,220,269 B1 | 5/2007 | Ansel et al. |
| 7,232,452 B2 * | 6/2007 | Adams ............... A61F 2/013 606/200 |
| 7,252,674 B2 | 8/2007 | Wyzgala et al. |
| 7,323,002 B2 | 1/2008 | Johnson et al. |
| 7,374,561 B2 | 5/2008 | Barbut |
| 7,399,307 B2 | 7/2008 | Evans et al. |
| 7,645,261 B2 | 1/2010 | Hinchliffe |
| 7,645,296 B2 | 1/2010 | Theron et al. |
| 7,691,121 B2 | 4/2010 | Rosenbluth et al. |
| 7,731,683 B2 | 6/2010 | Jang et al. |
| 7,909,801 B2 | 3/2011 | Hinchliffe |
| 8,100,935 B2 | 1/2012 | Rosenbluth et al. |
| 8,162,878 B2 | 4/2012 | Bonnette et al. |
| 8,292,914 B2 | 10/2012 | Morsi |
| 8,409,237 B2 | 4/2013 | Galdonik et al. |
| 8,425,549 B2 | 4/2013 | Lenker et al. |
| 8,435,218 B2 | 5/2013 | Hinchliffe |
| 8,475,487 B2 | 7/2013 | Bonnette et al. |
| 8,486,104 B2 | 7/2013 | Samson et al. |
| 8,784,441 B2 | 7/2014 | Rosenbluth et al. |
| 8,911,468 B2 | 12/2014 | Ogle et al. |
| 8,956,386 B2 | 2/2015 | Hauser et al. |
| 8,979,870 B2 | 3/2015 | Richardson |
| 9,067,063 B2 | 6/2015 | Chi et al. |
| 9,427,252 B2 | 8/2016 | Sos |
| 9,439,664 B2 | 9/2016 | Sos |
| 9,566,412 B2 | 2/2017 | Ulm, III et al. |
| 9,642,635 B2 | 5/2017 | Vale et al. |
| 9,814,477 B2 | 11/2017 | Jensen |
| 9,848,975 B2 | 12/2017 | Hauser |
| 10,016,266 B2 | 7/2018 | Hauser |
| 10,022,139 B2 | 7/2018 | Kobayashi et al. |
| 10,076,399 B2 | 9/2018 | Davidson |
| 10,080,575 B2 | 9/2018 | Brady et al. |
| 10,105,154 B1 | 10/2018 | Green |
| 10,130,387 B2 | 11/2018 | McRae et al. |
| 10,231,751 B2 | 3/2019 | Sos |
| 10,292,804 B2 | 5/2019 | Wang et al. |
| 10,383,644 B2 | 8/2019 | Molaei et al. |
| 10,433,867 B2 | 10/2019 | Kassab et al. |
| 11,622,781 B2 | 4/2023 | Behan |
| 2001/0011182 A1 | 8/2001 | Dubrul et al. |
| 2002/0013548 A1 | 1/2002 | Hinchliffe |
| 2002/0016624 A1 | 2/2002 | Patterson et al. |
| 2002/0049452 A1 | 4/2002 | Kurz et al. |
| 2002/0082558 A1 | 6/2002 | Samson et al. |
| 2002/0188313 A1 | 12/2002 | Johnson et al. |
| 2004/0006306 A1 | 1/2004 | Evans et al. |
| 2004/0006367 A1 | 1/2004 | Johnson et al. |
| 2004/0049169 A1 | 3/2004 | Fischell |
| 2004/0073243 A1 | 4/2004 | Sepetka et al. |
| 2004/0127885 A1 | 7/2004 | Barbut |
| 2004/0133232 A1 | 7/2004 | Rosenbluth et al. |
| 2004/0153110 A1 | 8/2004 | Kurz et al. |
| 2004/0158270 A1 | 8/2004 | Wyzgala et al. |
| 2005/0027236 A1 | 2/2005 | Douk |
| 2005/0197688 A1 | 9/2005 | Theron et al. |
| 2005/0277976 A1 | 12/2005 | Galdonik et al. |
| 2006/0041246 A1 | 2/2006 | Provost-Tine et al. |
| 2006/0041304 A1 | 2/2006 | Jang et al. |
| 2006/0189921 A1 | 8/2006 | Galdonik et al. |
| 2006/0229645 A1 | 10/2006 | Bonnette et al. |
| 2006/0264989 A1 | 11/2006 | Hinchliffe |
| 2007/0207179 A1 | 9/2007 | Andersen et al. |
| 2008/0015541 A1 | 1/2008 | Rosenbluth et al. |
| 2008/0086110 A1 | 4/2008 | Galdonik et al. |
| 2008/0103508 A1 | 5/2008 | Karakurum |
| 2008/0312681 A1 | 12/2008 | Ansel et al. |
| 2009/0156983 A1 | 6/2009 | Bonnette et al. |
| 2009/0171267 A1 | 7/2009 | Bonnette et al. |
| 2010/0082052 A1 | 4/2010 | Hinchliffe |
| 2010/0131000 A1 | 5/2010 | DeMello et al. |
| 2010/0145371 A1 | 6/2010 | Rosenbluth et al. |
| 2010/0222736 A1 | 9/2010 | Jang et al. |
| 2010/0256600 A1 | 10/2010 | Ferrera |
| 2011/0022075 A1 | 1/2011 | Christiansen et al. |
| 2011/0060298 A1 | 3/2011 | Saadat |
| 2011/0082493 A1 | 4/2011 | Samson et al. |
| 2011/0130778 A1 | 6/2011 | Hinchliffe |
| 2012/0046676 A1 | 2/2012 | Morsi |
| 2012/0271231 A1 | 10/2012 | Agrawal |
| 2013/0190855 A1 | 7/2013 | Wang et al. |
| 2014/0066969 A1 | 3/2014 | Eskridge |
| 2014/0135803 A9 | 5/2014 | Rosenbluth et al. |
| 2014/0200608 A1 | 7/2014 | Brady et al. |
| 2014/0243790 A1 | 8/2014 | Callaghan et al. |
| 2014/0257245 A1 | 9/2014 | Rosenbluth et al. |
| 2014/0276403 A1 | 9/2014 | Follmer et al. |
| 2014/0371769 A1 | 12/2014 | Vale et al. |
| 2014/0371778 A1 | 12/2014 | Rudakov et al. |
| 2015/0032147 A1 | 1/2015 | Janardhan et al. |
| 2015/0088190 A1 | 3/2015 | Jensen |
| 2015/0250497 A1 | 9/2015 | Marks et al. |
| 2015/0359547 A1 | 12/2015 | Vale et al. |
| 2016/0022296 A1 | 1/2016 | Brady et al. |
| 2016/0249942 A1 | 9/2016 | Olson |
| 2016/0249978 A1 | 9/2016 | Lee et al. |
| 2016/0256180 A1 | 9/2016 | Vale et al. |
| 2016/0271360 A1 | 9/2016 | Ulm, III |
| 2016/0338720 A1 | 11/2016 | Kassab et al. |
| 2016/0361077 A1 | 12/2016 | Marks et al. |
| 2017/0105743 A1 | 4/2017 | Vale et al. |
| 2017/0143938 A1 | 5/2017 | Ogle et al. |
| 2017/0215903 A1 | 8/2017 | Vale et al. |
| 2017/0238951 A1 | 8/2017 | Yang et al. |

(56) References Cited

U.S. PATENT DOCUMENTS

| | | |
|---|---|---|
| 2017/0303949 A1 | 10/2017 | Ribo Jacobi et al. |
| 2017/0333060 A1 | 11/2017 | Panian |
| 2017/0333076 A1 | 11/2017 | Bruzzi et al. |
| 2018/0104041 A1 | 4/2018 | Hauser |
| 2018/0140315 A1 | 5/2018 | Bowman et al. |
| 2018/0325647 A1 | 11/2018 | Hauser |
| 2018/0333248 A1 | 11/2018 | Davidson |
| 2018/0344248 A1 | 12/2018 | Zeng et al. |
| 2019/0029713 A1 | 1/2019 | McRae et al. |
| 2019/0133616 A1 | 5/2019 | Sachar et al. |
| 2019/0133628 A1 | 5/2019 | Follmer et al. |
| 2019/0167287 A1 | 6/2019 | Vale et al. |
| 2019/0269491 A1 | 9/2019 | Jalgaonkar et al. |
| 2020/0281612 A1 | 9/2020 | Kelly et al. |

FOREIGN PATENT DOCUMENTS

| | | |
|---|---|---|
| EP | 0385920 A2 | 9/1990 |
| EP | 0561903 A1 | 9/1993 |
| EP | 0630617 A1 | 12/1994 |
| EP | 0561903 B1 | 7/1995 |
| EP | 0820729 A1 | 1/1998 |
| EP | 0630617 B1 | 9/1998 |
| EP | 0961628 A1 | 12/1999 |
| EP | 0961628 A4 | 5/2000 |
| EP | 1007130 A1 | 6/2000 |
| EP | 1007130 A4 | 6/2000 |
| EP | 1007139 A1 | 6/2000 |
| EP | 1007139 A4 | 6/2000 |
| EP | 1026997 A1 | 8/2000 |
| EP | 1030603 A1 | 8/2000 |
| EP | 1105183 A1 | 6/2001 |
| EP | 1105183 A4 | 3/2002 |
| EP | 1241993 A1 | 9/2002 |
| EP | 1304965 A2 | 5/2003 |
| EP | 1030603 A4 | 6/2003 |
| EP | 1355692 A1 | 10/2003 |
| EP | 1408854 A1 | 4/2004 |
| EP | 0961628 B1 | 12/2004 |
| EP | 1561487 A2 | 8/2005 |
| EP | 1561487 A3 | 8/2005 |
| EP | 1026997 B1 | 10/2005 |
| EP | 1355692 A4 | 12/2005 |
| EP | 1105183 B1 | 1/2006 |
| EP | 1611855 A1 | 1/2006 |
| EP | 1677849 A1 | 7/2006 |
| EP | 1007130 B1 | 8/2006 |
| EP | 1691856 A2 | 8/2006 |
| EP | 1696966 A2 | 9/2006 |
| EP | 1241993 B1 | 3/2007 |
| EP | 1761298 A2 | 3/2007 |
| EP | 1561487 B1 | 4/2007 |
| EP | 1789121 A2 | 5/2007 |
| EP | 1791587 A1 | 6/2007 |
| EP | 2208483 A1 | 7/2010 |
| EP | 2319575 A1 | 5/2011 |
| EP | 2786717 A2 | 10/2014 |
| EP | 2786717 A3 | 11/2014 |
| EP | 2848211 A1 | 3/2015 |
| EP | 2851016 A1 | 3/2015 |
| EP | 3017775 A1 | 5/2016 |
| EP | 3020344 A1 | 5/2016 |
| EP | 3718492 A1 | 10/2020 |
| WO | WO-9306885 A1 | 4/1993 |
| WO | WO-9823319 A1 | 6/1998 |
| WO | WO-9823320 A1 | 6/1998 |
| WO | WO-9834673 A1 | 8/1998 |
| WO | WO-9836786 A1 | 8/1998 |
| WO | WO-9916362 A1 | 4/1999 |
| WO | WO-9923952 A1 | 5/1999 |
| WO | WO-0012169 A1 | 3/2000 |
| WO | WO-0145572 A1 | 6/2001 |
| WO | WO-0187168 A1 | 11/2001 |
| WO | WO-0209599 A2 | 2/2002 |
| WO | WO-0239912 A1 | 5/2002 |
| WO | WO-0209599 A3 | 7/2002 |
| WO | WO-02055146 A1 | 7/2002 |
| WO | WO-02087677 A2 | 11/2002 |
| WO | WO-03097122 A2 | 11/2003 |
| WO | WO-03097122 A3 | 6/2004 |
| WO | WO-2005011786 A1 | 2/2005 |
| WO | WO-2005039664 A2 | 5/2005 |
| WO | WO-2005039664 A3 | 6/2005 |
| WO | WO-2005046736 A3 | 10/2005 |
| WO | WO-2005118050 A2 | 12/2005 |
| WO | WO-2006023329 A2 | 3/2006 |
| WO | WO-2006032686 A1 | 3/2006 |
| WO | WO-2006023329 A3 | 4/2006 |
| WO | WO-2006110186 A2 | 10/2006 |
| WO | WO-2006110186 A3 | 6/2007 |
| WO | WO-2008086180 A1 | 7/2008 |
| WO | WO-2005118050 A3 | 1/2009 |
| WO | WO-2009154441 A1 | 12/2009 |
| WO | WO-2011008987 A3 | 5/2011 |
| WO | WO-2012156924 A1 | 11/2012 |
| WO | WO-2014039548 A1 | 3/2014 |
| WO | WO-2014113821 A1 | 7/2014 |
| WO | WO-2014188300 A1 | 11/2014 |
| WO | WO-2015189354 A1 | 12/2015 |
| WO | WO-2016071524 A1 | 5/2016 |
| WO | WO-2016113047 A1 | 7/2016 |
| WO | WO-2016126974 A1 | 8/2016 |
| WO | WO-2016138260 A1 | 9/2016 |
| WO | WO-2016138508 A1 | 9/2016 |
| WO | WO-2017074530 A1 | 5/2017 |
| WO | WO-2017097616 A1 | 6/2017 |
| WO | WO-2018033401 A1 | 2/2018 |
| WO | WO-2018107133 A1 | 6/2018 |
| WO | WO-2018107133 A8 | 8/2018 |
| WO | WO-2018169959 A1 | 9/2018 |
| WO | WO-2018222998 A1 | 12/2018 |
| WO | WO-2019007032 A1 | 1/2019 |
| WO | WO-2019027380 A1 | 2/2019 |
| WO | WO-2019051425 A1 | 3/2019 |
| WO | WO-2019094749 A1 | 5/2019 |
| WO | WO-2019094782 A1 | 5/2019 |
| WO | WO-2019168737 A1 | 9/2019 |
| WO | WO-2021016213 A1 | 1/2021 |
| WO | WO-2021151969 A1 | 8/2021 |

OTHER PUBLICATIONS

Donkor, Eric., Stroke in the 21st Century: A Snapshot of the Burden, Epidemiology, and Quality of Life, Stroke Research and Treatment, vol. 2018, Article ID 3238165 (2018).

Extended European Search Report dated Sep. 27, 2019 in EP Patent Application Serial No. 19167604.8.

Froehler, Michael, Comparison of Vacuum Pressures and Forces Generated by Different Catheters and Pumps for Aspiration Thrombectomy in Acute Ischemic Stroke, Intervent. Neurol, 6(3-4):199-206 (May 2017).

Garcia-Tornel, et al., When to Stop: Detrimental Effect of Device Passes in Acute Ischemic Stroke Secondary to Large Vessel Occlusion, Stroke, 50(7):1781-1788 (Jul. 2019).

International Search Report & Written Opinion dated Apr. 7, 2021 in Int'l PCT Patent Appl. Serial No. PCT/EP2021/051903 (0110).

International Search Report & Written Opinion dated Apr. 19, 2023 in Int'l PCT Patent Appl. Serial No. PCT/IB2023/050468 (0210).

Jin, et al., Association Between Extracranial Carotid Artery Tortuosity and Clinical Outcomes in Anterior Circulation Acute Ischemic Stroke Without Undergoing Endovascular Treatment, Journal of Stroke and Cerebrovascular Diseases, 29(2):104512 (Feb. 2020).

Kaymaz, et al., Influence of Carotid Tortuosity on Internal Carotid Artery Access Time in the Treatment of Acute Ischemic Stroke, Interventional Neuroradiology, 23(6):583-588 (Dec. 2017).

Mokin, et al., Semi-automated Measurement of Vascular Tortuosity and its Implications for Mechanical Thrombectomy Performance, Neuroradiology, 63(3):381-389 (Mar. 2021).

Mont'Alverne, et al., Unfavorable Vascular Anatomy During Endovascular Treatment of Stroke: Challenges and Bailout Strategies, Journal of Stroke: 22(2):185-202 (May 2020).

(56) References Cited

OTHER PUBLICATIONS

Pfaff, et al., Delivery Assist Catheters, a New Device Class and Initial Experience in Mechanical Thrombectomy in Acute Ischemic Stroke Patients, Clinical Neuroradiology, 29(4):661-667 (Dec. 2019).

Rosa, et al., Aortic and Supra-Aortic Arterial Tortuosity and Access Technique: Impact on Time to Device Deployment in Stroke Thrombectomy, Interventional Neuroradiology, 27(3):419-426 (Jun. 2021).

Sanchez, et al., ANCD Thrombectomy Device: In Vitro Evaluation, J. NeuroIntervent. Surg., 12(1):77-81 (Jan. 2020).

Snelling, et al., Unfavorable Vascular Anatomy Is Associated With Increased Revascularization Time and Worse Outcome in Anterior Circulation Thrombectomy, World Neurosurgery, 120:e976-83 (Dec. 2018).

Yeo, et al., Why Does Mechanical Thrombectomy in Large Vessel Occlusion Sometimes Fail?, Clinical Neuroradiology, 29(3):401-414 (Sep. 2019).

* cited by examiner

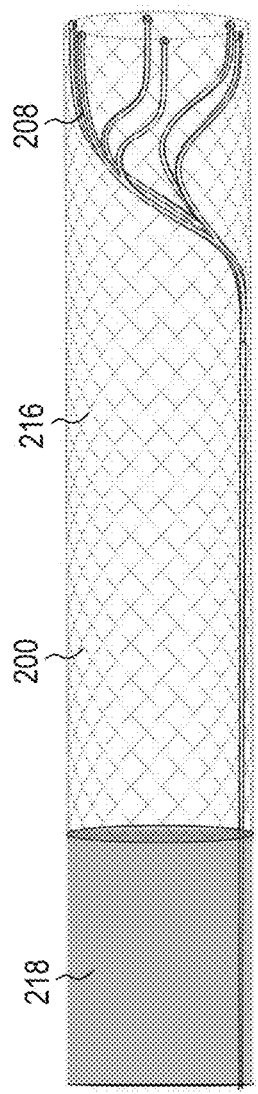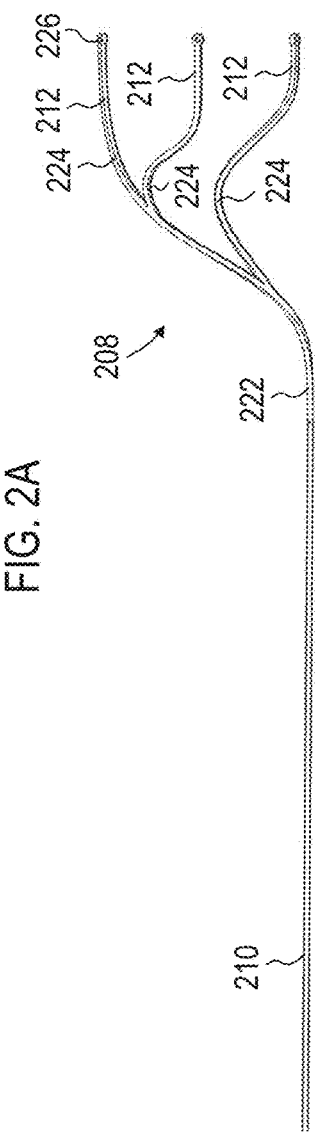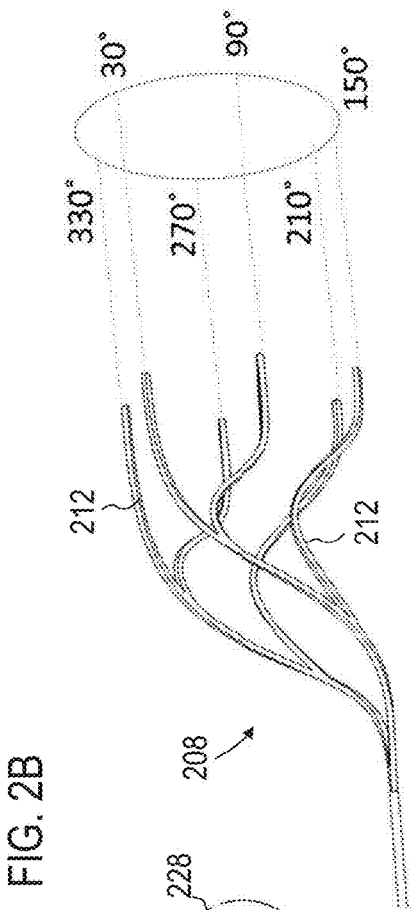

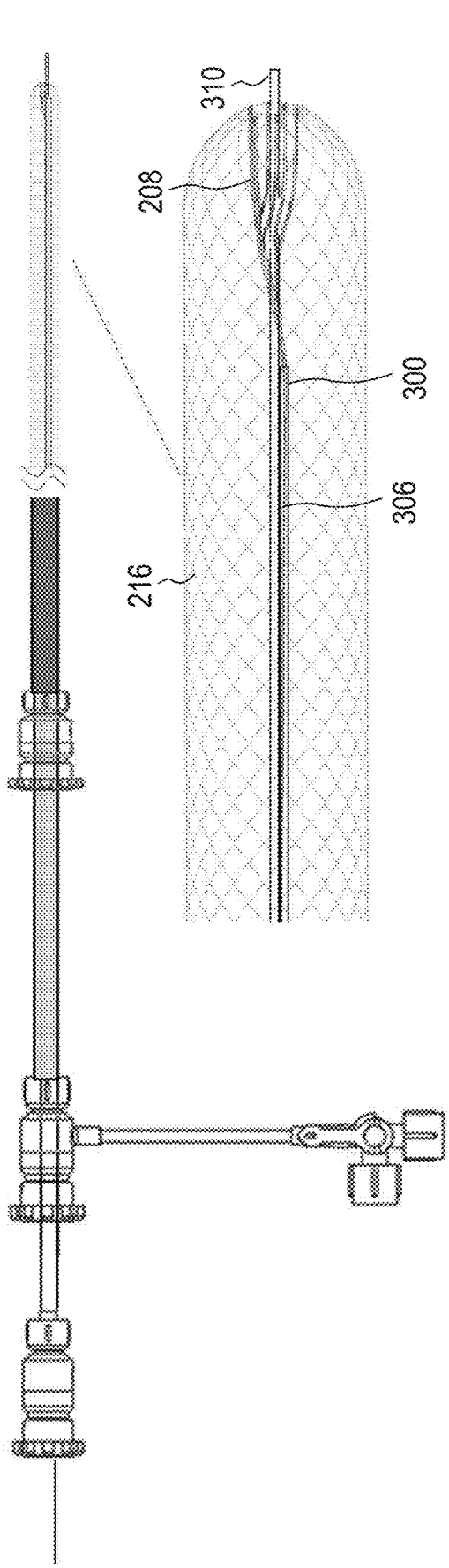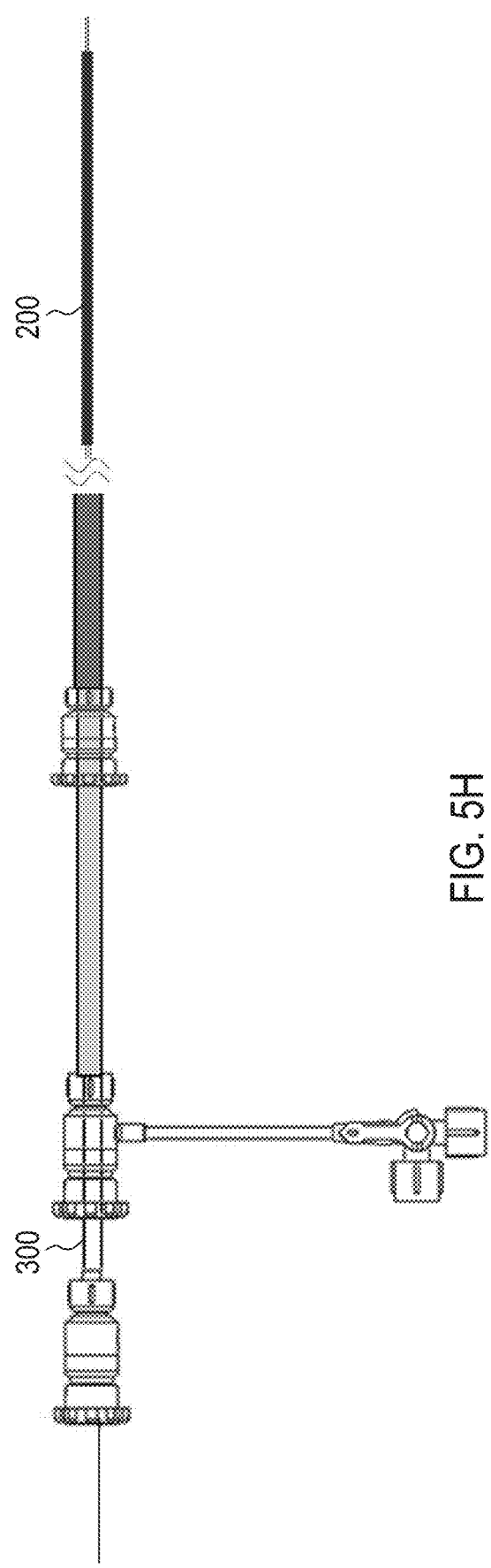
FIG. 5G
FIG. 5H

CATHETER FOR ACCESSING THE VASCULATURE INCLUDING THE NEUROVASCULATURE, AND METHODS OF USE

I. CROSS-REFERENCE TO RELATED APPLICATION

This application is a continuation of U.S. patent application Ser. No. 18/156,585, filed Jan. 19, 2023, now U.S. Pat. No. 11,737,767, which claims priority to U.S. Provisional Patent Application Ser. No. 63/267,032, filed Jan. 21, 2022, the entire contents of each of which are incorporated herein by reference.

II. TECHNICAL FIELD

This technology generally relates to catheter systems for removing an obstruction(s) from a blood vessel, for example, for retrieving a clot/thrombus in the neurovasculature for the treatment of stroke.

III. BACKGROUND

Ischemic stroke is caused by a partial or complete interruption to cerebral blood perfusion. Such an interruption may be caused by a thrombus or embolus, i.e. a clot, originating from a more proximal location within the bloodstream, becoming trapped within the narrowing intracranial vessels. The interruption of blood flow to a portion of the brain for any prolonged period of time results in a region of infarcted tissue, known as the core infarct, that is irreversibly damaged and grows larger with time. Infarcted regions of the brain will result in neurological deficits that may range from minor speech and coordination problems to total loss of muscle and cognitive control.

The oxygen-starved region around the core infarct also grows larger the longer the interruption continues. This region, known as the penumbra, may regenerate if blood perfusion is restored in a timely manner. This phenomenon of a treatable ischemic event has given rise to the phrase "time is brain," now common amongst associated clinicians.

In recent years, the technology for mechanical removal of such blockages has enabled reperfusion of blood flow and effective treatment of stroke in some cases. Within recent years, the first of several clinical studies were published that validated the efficacy of stent retrievers for blood flow restoration versus the standard of care at the time, which was intravenous thrombolysis medication and aspiration clot retrieval.

Mechanical clot retrieval devices are generally metal baskets or stents that are connected to a retrieval wire. During a clot removal procedure, a guide wire is placed across the length of the clot and a catheter is navigated over the guidewire to cross the clot. The clot retrieval device is delivered through the catheter to the required location. The catheter or sheath is retracted from over the clot retrieval device, which then expands and engages with the clot. The clot retrieval device and the clot integrated therein can then be removed through the blood vessel using tension by pulling the retrieval wire. Optionally, a suction catheter can be used to help with removal.

In many cases, the clot cannot be removed intact during the first pass of the clot retrieval device and multiple passes are required to get blood flow restoration. The improvement in first pass clot removal is a target of many current developments in this field of technology.

In practice, the clinician will use several different tools during the endovascular procedure to remove the clot. Generally, a guidewire will be placed into the femoral artery using the modified Seldinger technique and will be navigated through the carotid artery into the cerebral vasculature of the brain.

The guidewire is then pushed through the clot. Once the guidewire is in place, a very narrow tubular catheter known as a microcatheter (approx. 0.4 mm diameter) is advanced to the distal side of the clot over the wire.

The guidewire is then removed and a stent retriever is pushed through the microcatheter and deployed along the length of the clot. The stent retriever engages with the clot and is then retracted to remove the clot from the circulatory system of the patient. In most cases, this procedure is carried out while simultaneously applying aspiration through a larger diameter catheter that is navigated close to the clot over the microcatheter. The aspiration catheter is stiffer than the microcatheter due to its larger diameter and reinforcement, which is required to prevent collapse during suction. The microcatheter is therefore also required as a support and guide for introduction of the aspiration catheter through the vasculature.

European Patent Application Pub. No. EP 3718492 A1 discloses a catheter apparatus for the removal of a clot from the circulatory system of a patient in which a plurality of clot-engaging elements are deployable independently from each other. In this way, the first pass clot removal rate can be improved.

In addition to the above technique, there have been multiple different approaches described using the combination of stent retriever and aspiration catheter. Some of these techniques describe the complete withdrawal of stent retriever and clot into the aspiration catheter. Other approaches are directed to the withdrawal of the clot and stent retriever using the aspiration catheter, wherein the proximal part of the clot is attached to the aspiration catheter during the removal.

The clot retrieval approach chosen is often influenced by the clot composition and in some cases where the clot is very soft thrombus, an aspiration catheter alone may be sufficient to remove the entire clot via suction. In this case, a microcatheter is still required for support to help with navigation of the aspiration catheter to the desired site.

Regardless of the specific technique used, removal of the clot without delay is crucially important. Although the guidewire and microcatheter are generally advanced to the clot quickly, the positioning of the aspiration catheter may be a limiting factor. The process of advancing the aspiration catheter becomes particularly difficult after passing through the internal carotid artery. This is due to the narrow and tortuous vessels after this point in the cerebral vasculature and is exacerbated in older patients where the vasculature is diseased and elongated. This time-consuming part of the procedure may impact the patient's clinical outcome. In the case where the clot is not removed during the first pass, the cumulative time taken during multiple attempts can be significant.

Devices have been described with a distally expanding funnel at the distal end of the aspiration catheter. These devices are generally separate to the aspiration catheter and are fed through the lumen and pushed out of the distal end of the aspiration catheter to expand. Such devices are intended to widen the already large luminal diameter of the aspiration catheter and to engulf a withdrawing stent retriever and/or clot to ensure no microemboli are released during the clot removal. WO 02/087677 A2, U.S. Patent App. Pub. No. 2017/0303949 to Ribo Jacobi, WO 2016/113047 A1, U.S. Patent App. Pub. No. 2019/0269491 to Jalgaonkar, U.S. Patent App. Pub. No. 2017/0333060 to Panian are examples of documents directed to this kind of technique.

U.S. Pat. No. 6,632,236 to Hogendijk describes apparatus for occluding a vessel and enhancing blood flow within a catheter. The catheter includes a multi-section self-expanding wire weave forming a radially expandable body and an occlusive distal section, covered with an elastomeric polymeric coating, and disposed within an outer sheath.

U.S. Pat. No. 6,929,634 to Dorros describes apparatus and methods for treatment of stroke using a catheter having a distal occlusive member in the common carotid artery of the hemisphere of the cerebral occlusion. Retrograde flow is provided through the catheter to effectively control cerebral flow characteristics. Under such controlled flow conditions, a thrombectomy device is used to treat the occlusion, and any emboli generated are directed into the catheter.

U.S. Pat. No. 6,206,868 to Parodi discloses an occlusive element with a self-expanding wire mesh basket covered with an elastomeric polymer coating. The catheter is initially surrounded by a movable sheath, and is inserted transluminally with the sheath at a distalmost position. The sheath is retracted proximally to cause the basket to deploy, and the basket is again collapsed within the sheath by moving the sheath to its distal-most position.

U.S. Patent App. Pub. No. 2017/0238951 to Yang describes a neurovascular catheter for distal neurovascular access or aspiration. The catheter includes an elongate flexible tubular body, having a proximal end, a distal end, and a side wall defining a central lumen. A distal zone of the tubular body includes a tubular inner liner, a tie layer separated from the lumen by the inner liner, a helical coil surrounding the tie layer, an outer jacket surrounding the helical coil, and an opening at the distal end. Adjacent windings of the helical coil are spaced progressively further apart in the distal direction. The opening at the distal end of the tubular body is enlargeable from a first inside diameter for transluminal navigation to a second, larger inside diameter to facilitate aspiration of thrombus into the lumen.

U.S. Patent App. Pub. No. 2017/0143938 to Ogle describes a suction catheter system is described with a suction nozzle that can extend from a guide catheter of the like. The suction nozzle can be positioned by tracking the suction nozzle through a vessel while moving a proximal portion of the suction extension within the lumen of the guide catheter. A suction lumen extends from the proximal end of the guide catheter through at least part of the guide catheter central lumen and through the suction tip.

U.S. Patent App. Pub. No. 2016/0256180 to Vale describes a rapid exchange (RX) catheter that provides a proximal seal against a guide catheter inner lumen so that aspiration may be applied through a guide catheter. The catheter may include an exit port that defines a transfer port for aspiration and may enable minimal frictional engagement with the guide catheter proximal of the exit port. Aspiration can be applied to the lumen of the guide catheter and may be directed to and effective at the tip of the RX aspiration catheter. A tip of the RX catheter may facilitate aspiration and retrieval of the clot by expanding under load and can also partially or fully occlude the vessel.

WO 2017/097616 A1 discloses a plurality of devices and methods for removing blockages from blood vessels. A stent retriever is first deployed via a microcatheter and, to improve the clot removal process, an aspiration catheter is then advanced to the position of the clot. A clot receptor device is deployed, which circumferentially seals against a distal section of the aspiration catheter, such that the stent retriever and the clot may be aspirated through the tapered opening of the receptor device during the removal process. The stent retriever may also deployed using the microcatheter and an aspiration catheter is then forwarded to the position of the clot to aspirate the stent retriever and the clot.

U.S. Pat. No. 8,425,549 to Lenker discloses a catheter having a distal portion, which can be radially expanded by means of a coil or a helical ribbon that is distally displaceable within the catheter. The expanded configuration allows applying a negative pressure through the lumen of the catheter to aspirate obstructive matter through the distal end opening and into the lumen of the catheter.

Further devices for neurovascular endoluminal intervention of the kind as indicated are disclosed in WO 2016/126974, WO 2018/169959, and WO 98/23320.

Besides the above-described catheter devices, introducer sheaths are known, which are short cannula-like devices that are used for vessel access. They are inserted into the target vessel percutaneously and a central dilator is then removed to allow access for insertion of other devices such as guidewires and catheters. Recently a number of introducer devices have been developed that have the capability to expand to accommodate devices larger than the nominal vessel size. Examples of expanding sheath type devices are the Edwards eSheath™ and the Terumo Solopath™.

In view of the foregoing, there is a need for a catheter that is sufficiently small and flexible to permit navigation through small and/or tortuous vessels (e.g., the neurovasculature) while sufficiently robust to remove an obstruction such as a clot/thrombus. WO 2021/1151969, the entire contents of which are incorporated herein by reference, describes improved catheters for neurovascular endoluminal intervention, e.g., for the treatment of ischemic stroke, that overcomes many of the drawbacks of the foregoing. It would be beneficial to provide improved designs for easily expanding a catheter for obstruction removal and collapsing such a catheter for delivery and removal within the vasculature.

IV. SUMMARY

Provided herein are systems and methods for removing an obstruction(s) from a blood vessel. For example, an improved catheter is provided that is sufficiently small and flexible to permit navigation through small and/or tortuous vessels (e.g., the neurovasculature) while being sufficiently robust to remove an obstruction such as a clot/thrombus (e.g., via aspiration through the catheter). The catheter is designed to be easily expandable for obstruction removal and collapsible for delivery and removal within the vasculature.

In accordance with some aspects, a catheter is provided for removing an obstruction from a blood vessel. The catheter may include an elongated tube, an actuator tube disposed within the elongated tube, and an actuation wire disposed within the actuator tube. The elongated tube may be transitionable between an expanded state and a collapsed state. For example, the elongated tube may be sized and shaped to be advanced through the blood vessel to the obstruction in the collapsed state. The actuation wire may include an elongated shaft coupled to a plurality of struts via an articulation region. The distal end of each one of the plurality of struts may be affixed about a circumference of the distal end of the elongated tube. The actuator tube and the actuation wire may be used to transition the elongated tube between the collapsed and expanded states. For example, translation of the actuator tube relative to the actuation wire may cause the plurality of struts to expand radially outward to transition the elongated tube to the expanded state, thereby permitting removal of the obstruction from the blood vessel.

The elongated tube may include a braided material that may have an expandable biocompatible coating (e.g., an elastomer). The elongated tube may be collapsible via longitudinal force at the distal end of the elongated tube such that the elongated tube is longer in the collapsed state than in the expanded state.

The catheter may include an intermediate tube slidably positioned between the elongated tube and the actuator tube. The distal portion of the intermediate tube may be advanced distally within the elongated tube to reinforce the elongated tube for removal of the obstruction. A distal region of the intermediate tube may include a metal coil that may have a biocompatible coating.

The catheter may include a vacuum source to apply suction within the elongated tube to suck the obstruction into the elongated tube while in the expanded state to remove the obstruction from the blood vessel. For example, the vacuum source may be coupled to the intermediate tube that is disposed within the elongated tube during application of suction such that the obstruction is sucked into the lumen of the intermediate tube.

The actuator tube and the actuation wire may maintain the elongated tube in the collapsed state during delivery and also cause the elongated tube to transition from the expanded state to the collapsed state after removal of the obstruction from the blood vessel such that the catheter system is removable from a subject in the collapsed state. Each strut of the plurality of struts may have a curvature to facilitate even collapse of the actuation wire. In some embodiments, the curvature ensures that a distance from a distal tip of each strut to an apex of the actuation wire proximal to the plurality of struts is the same. The articulation region of the actuation wire may include a branched structure. Each strut of the plurality of struts may include an eyelet at a distal tip for coupling to the elongated tube. The elongated wire may be offset from a central longitudinal axis of the elongated tube in the expanded state. Distal ends of the plurality of struts may be spaced apart equidistant about the circumference of the distal end of the elongated tube. The actuation wire may be formed of nitinol.

The actuator tube may be a dual lumen microcatheter having a guidewire lumen configured to receive a guidewire. The guidewire lumen may extend more distally than an actuation lumen for the actuation wire in the actuator tube.

The distal end of the catheter may be sized and shaped to be navigated to the blood vessel within a brain. For example, the distal end of the catheter may be sized and shaped to be navigated to a middle cerebral artery within the brain.

In accordance with some aspects, a method for removing an obstruction from a blood vessel using a catheter is provided. The method may include advancing a distal end of an elongated tube in a collapsed state through a blood vessel to the obstruction while an actuator tube is disposed within the elongated tube; translating an actuator tube relative to an actuation wire to cause a plurality of struts of the actuation wire to expand radially outward to transition the elongated tube to an expanded state within the blood vessel, wherein a distal end of each one of the plurality of struts is affixed about a circumference of the distal end of the elongated tube; and removing the obstruction from the blood vessel using the elongated tube while in the expanded state. The method may include translating the actuator tube relative to the actuation wire to cause the plurality of struts of the actuation wire to collapse radially inward to transition the elongated tube to the collapsed state within the blood vessel. The method may include translating an intermediate tube within the lumen of the elongated tube (e.g., after the actuator tube has been removed from the elongated tube) such that the intermediate tube moves into the expanded distal region of the elongated tube to reinforce the distal region for obstruction removal (e.g., via aspiration).

V. BRIEF DESCRIPTION OF THE FIGURES

The foregoing and other objects, features, and advantages of the description set forth herein will be apparent from the following description of particular embodiments of those inventive concepts, as illustrated in the accompanying drawings. It should be noted that the drawings are not necessarily to scale; emphasis instead is placed on illustrating the principles of the inventive concepts. Also, in the drawings, like reference characters may refer to the same parts or similar parts throughout the different views. It is intended that the embodiments and figures disclosed herein are to be considered illustrative rather than limiting.

FIG. 2A shows the distal region of an elongated tube of the catheter for an exemplary embodiment having a collapsible and expandable braided section using a self-collapsing/expanding mechanism.

FIG. 2B shows the distal region of an exemplary mechanism for self-collapsing/expanding the distal region (e.g., the braided section) of the elongated tube.

FIGS. 2C and 2D are perspective views of the exemplary mechanism of FIG. 2B.

FIGS. 5A through 5H show steps for transitioning an exemplary catheter between a collapsed state and an expanded state.

VI. DETAILED DESCRIPTION

Provided herein are systems and methods for removing an obstruction(s) from a blood vessel. For example, an improved catheter may be used for the treatment of ischemic stroke, which allows an overall easier and faster removal of a clot from a blood vessel.

The catheter has a collapsed state where the distal outer section is adapted to be easily navigated through the vasculature including through small and/or tortuous vessels (e.g., the neurovasculature). The catheter may then, preferably reversibly, be changed to an expanded state whereby the distal outer section is expanded to a wider diameter, which may be approximately equivalent to the diameter of the proximal outer section. This approach enables the catheter to be easily and rapidly navigated to the target site and subsequently dilated to facilitate removal of the one or several clots by aspiration. Using this design, a clinician does not waste valuable time navigating a large aspiration catheter through tortuous vessels. In addition, a microcatheter and an aspiration catheter may be combined into a single catheter, which also represents cost savings.

Figure 1A:
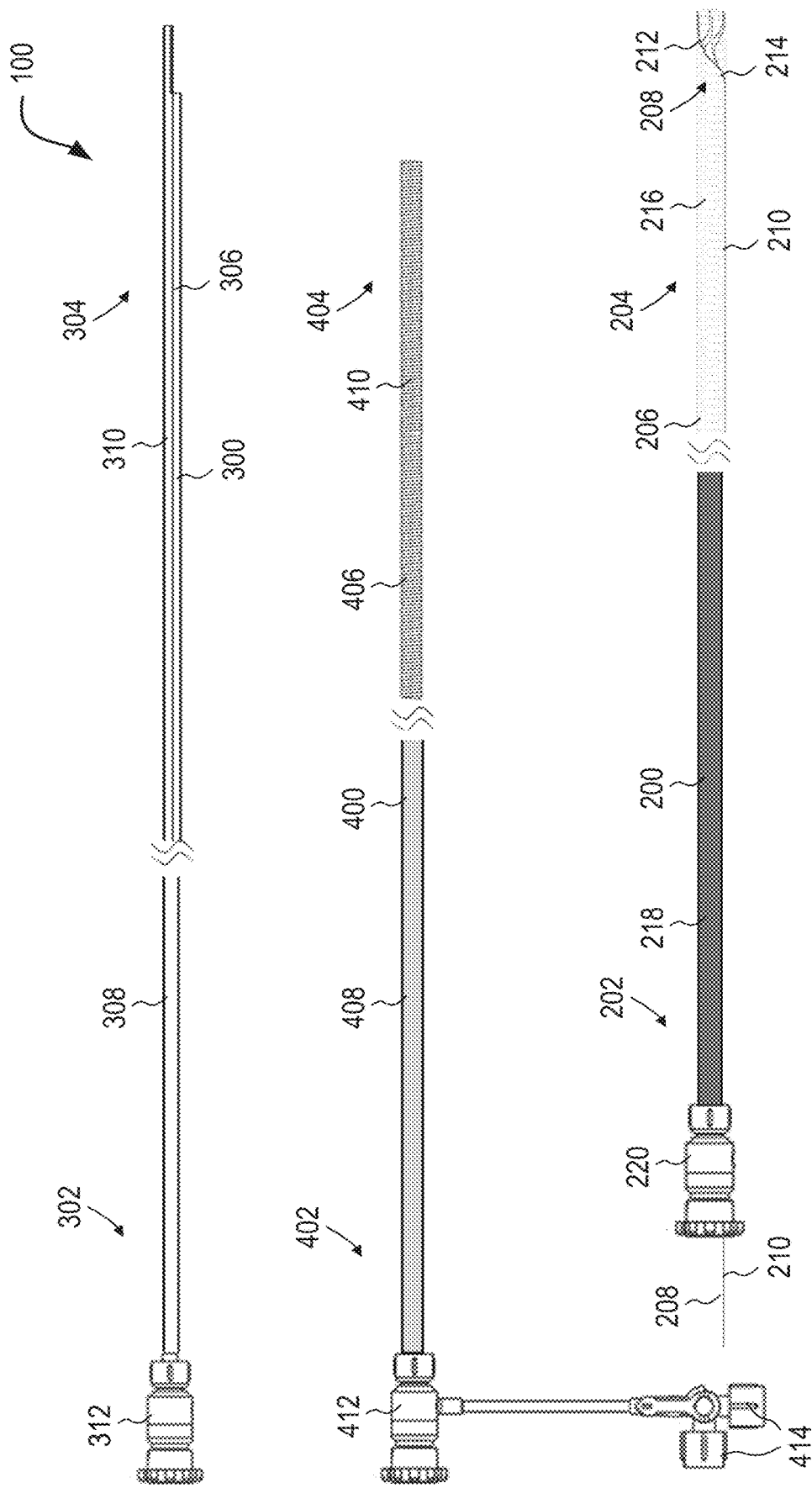
FIG. 1A shows exemplary components of a catheter for removing an obstruction(s) from a blood vessel.

Referring to FIG. 1A, an exemplary catheter is shown that may be used for removing an obstruction(s) from a blood vessel, for example, to treat a stroke. Catheter 100 illustratively includes elongated tube 200 that is transitionable between an expanded state and a collapsed state. Elongated tube 200 has proximal region 202, distal region 204, and lumen 206 extending therebetween. Elongated tube 200 is sized and shaped to be advanced through the blood vessel to the obstruction in the collapsed state.

To transition elongated tube 200 between the collapsed state and the expanded state, actuation wire 208 is provided. As illustrated, actuation wire 208 may include elongated shaft 210 coupled to a plurality of struts 212 via articulation region 214. The distal end of each one of the plurality of struts 212 may be affixed about a circumference of the distal end of elongated tube 200. Actuation wire 208 preferably has a length longer than elongated tube 200. As such, actuation wire 208 may be coupled to the distal end of elongated tube and extend out the proximal end, as shown in FIG. 1A, for manipulation by the clinician.

The portion of elongated tube 200 at distal region 204 is preferably formed of a contractible and expandable material such as a coil, a laser-cut tube, or braid 216 as illustrated. Distal region 204 may be coated with an expandable biocompatible material such as an elastomer. For example, the collapsible/expandable portion of elongated tube 200 may be an elastomer coated braid or coil. Proximal region 202 may be formed of a different material than distal region 204. For example, proximal region 202 may include shaft 218 formed from a polymer known in the art of catheter design. The diameter of proximal region 202 may be fixed such that only distal region 204 has a variable diameter. The elastomer coated braid or coil may be bonded to proximal region 202, for example, via an adhesive. Elongated tube 200 may include hemostasis valve 220 at the proximal end to permit insertion of additional interventional devices into lumen 206 of elongated tube and to close off proximal end of lumen 206 when hemostasis valve 220 is closed.

Preferably, shaft 218 of elongated tube 200 is flexible. Distal region 204 (illustratively, braid 216) is particularly flexible to permit navigation through the vasculature, including through small and/or tortuous vessels.

Catheter 100 further may include actuator tube 300, which is sized and shaped to be disposed within elongated tube 200. Actuator tube 300 includes proximal region 302, distal region 304, and lumen 306 extending therebetween. Lumen 306 is sized and shaped to receive actuation wire 208 therethrough. Preferably, actuator tube 300 has a length longer than the shaft of elongated tube 200, although actuation wire 208 is preferably longer than actuator tube 300.

Actuator tube 300 works together with actuation wire 208 to cause distal region 204 of elongated tube 200 to transition between the collapsed state and the expanded state. This provides a self-collapsing mechanism for easy and repeatable transition between these states. For example, translation of actuation wire 208 relative to actuation tube 300 causes the plurality of struts 212 to expand radially outward to transition elongated tube 200 to the expanded state, thereby permitting removal of the obstruction from the blood vessel.

Actuator tube 300 may function as a microcatheter. Shaft 308 at proximal region 302 may be relatively stiff, e.g., a hypotube. The diameter of actuator tube 300 may be fixed such that actuator tube 300 is not expandable. Distal region 304 is preferably more flexible than proximal region to permit bending and navigation through tortuous vessels. Actuator tube 300 may include guidewire lumen 310 to receive a guidewire therethrough. As illustrated, actuator tube 300 may be a dual lumen microcatheter having both guidewire lumen 310 and lumen 306 for receiving actuation wire 208 there through. Guidewire lumen 310 may extend more distally in the shaft than actuation lumen 306 for actuation wire 208 in actuator tube 300.

Actuator tube 300 may include hemostasis valve 312 at the proximal end to permit insertion of additional interventional devices (e.g., guidewire, actuation wire) into a lumen(s) of actuator tube 300 and to close off proximal end of lumens 306 and/or 310 when hemostasis valve 312 is closed.

Catheter 100 further may include intermediate tube 400, which is sized and shaped to be disposed within elongated tube 200. Intermediate tube 400 includes proximal region 402, distal region 404, and lumen 406 extending therebetween. Lumen 406 is sized and shaped to receive actuator tube 300 therethrough. Preferably, intermediate tube 400 has a length less than actuator tube 300, but longer than the shaft of elongated tube 200, although actuation wire 208 is preferably longer than intermediate tube 400.

Intermediate tube 400 is slidably disposed within elongated tube 200. For example, the distal end of intermediate tube 400 may be positioned proximally to the distal end of elongated tube 200 during delivery so as to maintain the low profile of catheter 100. Once suitable positioning is achieved in proximity to the obstruction in the blood vessel and elongated tube 200 has been transitioned to the expanded state, intermediate tube 400 may be advanced distally within elongated tube 200 to reinforce elongated tube 200 for removal of the obstruction.

Proximal region 402 may be formed of a different material than distal region 404. For example, proximal region 402 may include shaft 408 formed from a polymer known in the art of catheter design to provide flexibility. Distal region 404 may include a coil 410 (e.g., biocompatible metal such as nitinol or stainless steel) having a biocompatible coating (e.g., PTFE). Coil 410 may be tightly wound such that adjacent turns in the coil contact one another. The diameter of intermediate tube 400 may be fixed such that intermediate tube 400 is not expandable. Intermediate tube 400 may include hemostasis valve 412 at the proximal end to permit insertion of additional interventional devices (e.g., actuator tube 300) into lumen 406 of intermediate tube 400 and to close off the proximal end of lumen 406 when hemostasis valve 412 is closed. One or more additional valves 414 may be connected to the proximal end of intermediate catheter 400, for example, to permit coupling to a vacuum source for aspiration of the obstruction in the blood vessel via catheter 100.

Figure 1B:
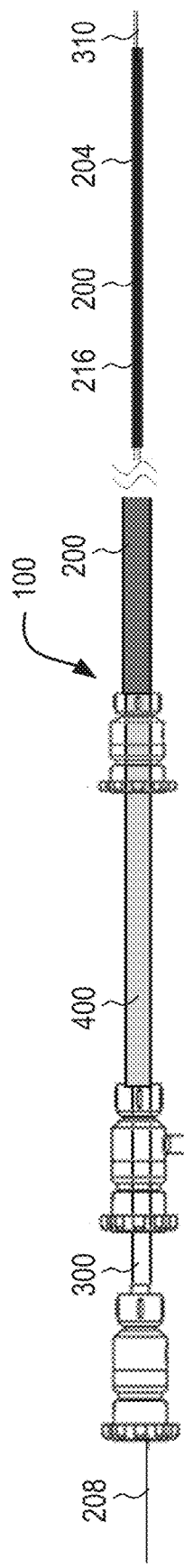
FIGS. 1B and 1C show, respectively, the catheter in the collapsed state and the expanded state.
Figure 1C:
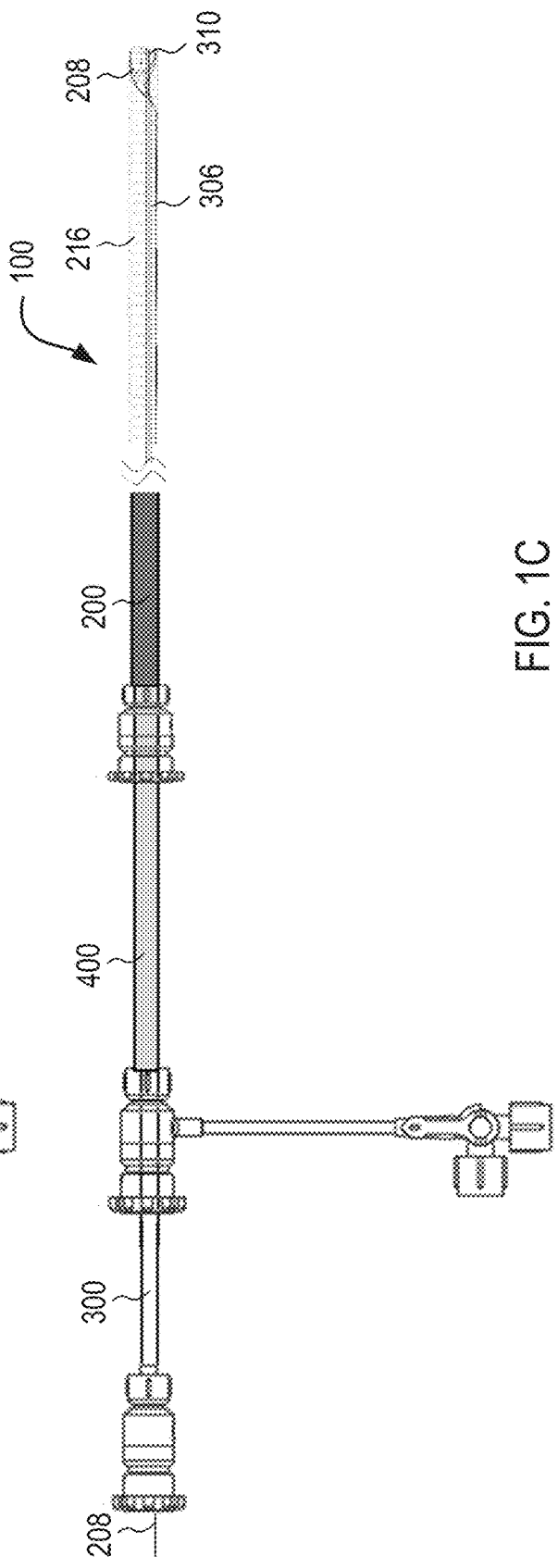

Referring now to FIGS. 1B and 1C, catheter 100 is shown, respectively, in a collapsed state and an expanded state. Actuator tube 300 is actuated to cause catheter 100 to transition from the collapsed state to the expanded state, and then may be further actuated cause catheter 100 to transition from the expanded state to the collapsed state. Actuator tube 300 may be moved in one direction (e.g., proximally) relative to actuation wire 208 to actuate the transition from collapsed to expanded and may be moved in another direction (e.g., distally) relative to actuation wire 208 to actuate the transition from expanded to collapsed. For example, actuator tube 300 may be unlocked by the clinician and moved proximally while elongated shaft 200 and intermediate tube 400 remain in place to cause distal region 204 (e.g., braid 216) of elongated shaft to expand. As such, elongated tube 200 is collapsible via longitudinal force at the distal end of elongated tube 200. As shown, elongated tube 200 is longer in the collapsed state than in the expanded state.

In this manner, the braided distal end of catheter 100 may be collapsed by being elongated. Braid elongation may be generally achieved by applying a longitudinal force to the distal end of the braided section. Conversely, the braid expansion may be achieved by releasing the longitudinal force. Advantageously, the distal end of elongated tube 200 may be held in place during expansion to prevent the catheter tip from jumping back upon the release of force. The self-collapsing mechanism allows force to be applied to the distal end of the braid as well as holding the distal end in place during expansion. As further advantages, these mechanisms allow advancing actuator tube 300 (e.g., a microcatheter) towards the distal end of elongated tube 200 to taper the diameter of the distal lumen and using actuator tube 300 to subsequently elongate braid 216 to narrow/collapse the entire distal braided section. As such, braid 216 may be collapsed onto actuator tube 300 to provide the sizing and flexibility of a microcatheter for delivery and removal of catheter 100.

Catheter 100 is preferably adapted to be inserted into the femoral artery of an adult human patient and to be navigated to the brain, for example to the middle cerebral artery, of the patient. Thus, the length of the catheter is preferably such that the catheter at least extends from the femoral artery of an adult human patient to the brain, in particular to the middle cerebral artery, of the same patient, to outside the patient for manipulation at the proximal end by the clinician. Depending on the application (e.g. in animals or humans, in children, female or male adults, etc.), catheter 100 preferably has an overall length of at least 30 cm, more preferably of at least 40 cm. For the use in humans, in particular in adult humans, the overall length of the catheter is preferably in a range between 100 cm and 200 cm, more preferably in a range between 130 cm and 180 cm.

The sizing of catheter 100 may be optimized for navigation in the neurovasculature. For example, the outer diameter of the shape-changing section distal section (e.g., the braided section) of elongated tube may be 0.5-6 mm in the collapsed state and 1-10 mm in the expanded state. In addition, the length of the shape-changing section distal section of elongated tube may be at least 10 cm from the distal end of elongated tube 200, such as 10-25 cm total, and may reduce about 5-25% in length when transitioned to the expanded state as compared to the collapsed state. In some embodiments, the diameter at the distal region of actuator tube 300 may be 0.4-2 mm for the dual lumen microcatheter configuration. The outer diameter of intermediate tube 400 may be 1-10 mm with an inner diameter of 0.8-8 mm. The length of the coiled section of intermediate tube 400 may extend at least 10 cm from the distal end of intermediate tube 400.

Referring now to FIG. 2A, a view of an exemplary distal region of elongated tube 200 is shown. Elongated tube 200 may include braid 216 at the distal end and shaft 218 coupled to braid 216 more proximally. Actuation wire 208 is shown to facilitate self-collapse/expansion of the distal end of elongated tube 200 (e.g., the entire braided section). In some embodiments, the self-collapse/expansion mechanism (actuation wire 208) is mounted to the distal end of the braided structure to facilitate a reduction in the braid diameter by enabling the clinician to both collapse the distal braid and to elongate the braid by applying a force longitudinally to the distal end of the braid.

FIG. 2B shows the distal region of an exemplary mechanism for self-collapsing the distal region of the elongated tube. Actuation wire 208 illustratively includes elongated shaft 210 coupled to struts 212 via articulation region 214. Actuation wire 208 may be formed from biocompatible metal such as nitinol or stainless steel and may exhibit shape memory characteristics. In some embodiments, actuation wire 208 is formed from nitinol wire. Actuation wire 208 may be formed of nitinol wire with distal multi-armed nitinol, as shown. Actuation wire 208 may be formed from a single piece of nitinol or from a plurality of nitinol pieces coupled together. For example, struts 212 may be laser cut from a single nitinol tube and coupled to the nitinol wire at apex 222, for example, via welding. Struts 212 may be configured to self-expand when actuated, for example, when exposed from the lumen of the actuator tube. Each strut 212 may have curvature 224 to facilitate even collapse of actuation wire 208. In some embodiments, curvature 224 of each strut 212 ensures that the distance from distal tip 226 of each strut 212 to apex 222 of actuation wire 208 is the same. Apex 222 preferably begins proximal to plurality of struts 212. Struts 212 may each have an S-shape. For example, the upper-most struts may form an S-shape with elongated shaft 210 and have one or more additional struts branch off the upper-most struts in S-shape form, as shown. There may be multiple upper-most struts, for example, two as shown in FIG. 2C. In some embodiments, struts 212 to not make a complete circle around the circumference at the distal end of the elongated tube. For example, there may be a gap between the struts (e.g., upper-most struts shown in FIG. 2C). In this manner, articulation region 214 may have a branched structure and, in some embodiments, the branches have multiple branches extending therefrom forming their own distinct networks of branches.

Referring now to FIG. 2C, a perspective view of the distal region of actuation wire 208 is shown. Struts 212 may be arranged circumferentially to connect to the inner lumen of the elongated tube (e.g., the braid). Elongated shaft 210 may be offset from a central longitudinal axis of the elongated tube in the expanded state. This ensures that elongated shaft 210 does not occlude the lumen of the elongated tube. Each strut 212 may include a coupling mechanism to couple to the distal end of the elongated tube. For example, each strut 212 may include eyelet 228 at its distal tip to facilitate connection to the braid.

As shown in FIG. 2D, distal ends of struts 212 may be spaced apart equidistant such that the struts are spaced apart about the circumference of the distal end of the elongated tube. As illustrated, there may be six struts spaced apart 60 degrees from one another.

Figure 3:
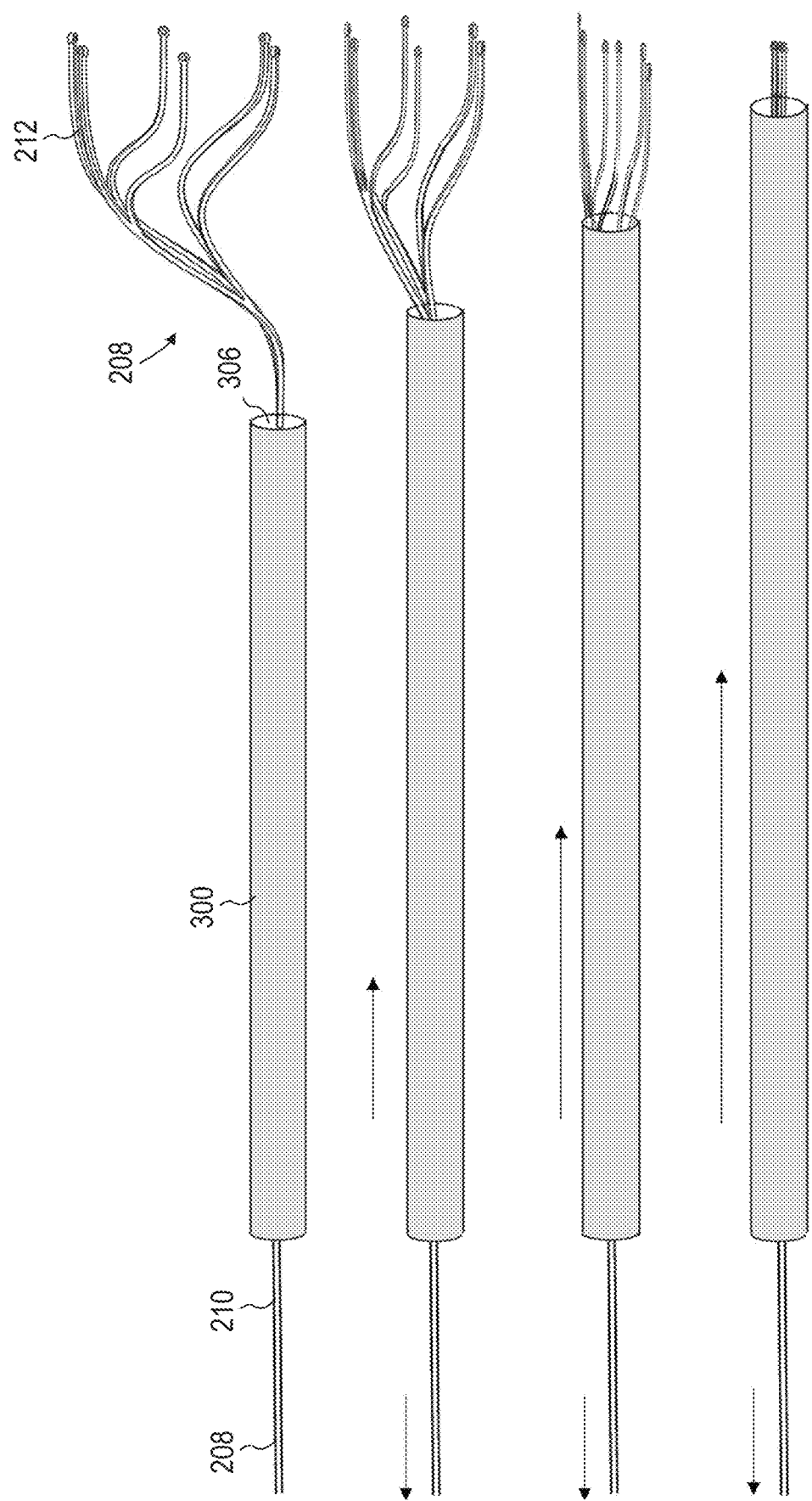
FIG. 3 shows exemplary steps for self-collapsing the collapsible portion of the elongated tube using an actuator tube and actuation wire system.

FIG. 3 illustrates exemplary steps for self-collapse using the actuation mechanisms. For example, as actuator tube 300 is advanced relative actuation wire 208, actuation wire 208 is drawn into lumen 306 of actuator tube 300. This causes the distal multi-armed strut structure to collapse radially inwards to transition to the collapsed state. As shown, curvature in the struts ensures equal circumferential collapse force. Actuator tube 300 may be advanced distally while actuation wire 208 is held in place, actuation wire 208 may be moved proximally while actuator tube is held in place, or actuator tube 300 may be advanced distally while actuation wire 208 is moved proximally.

Figure 4:
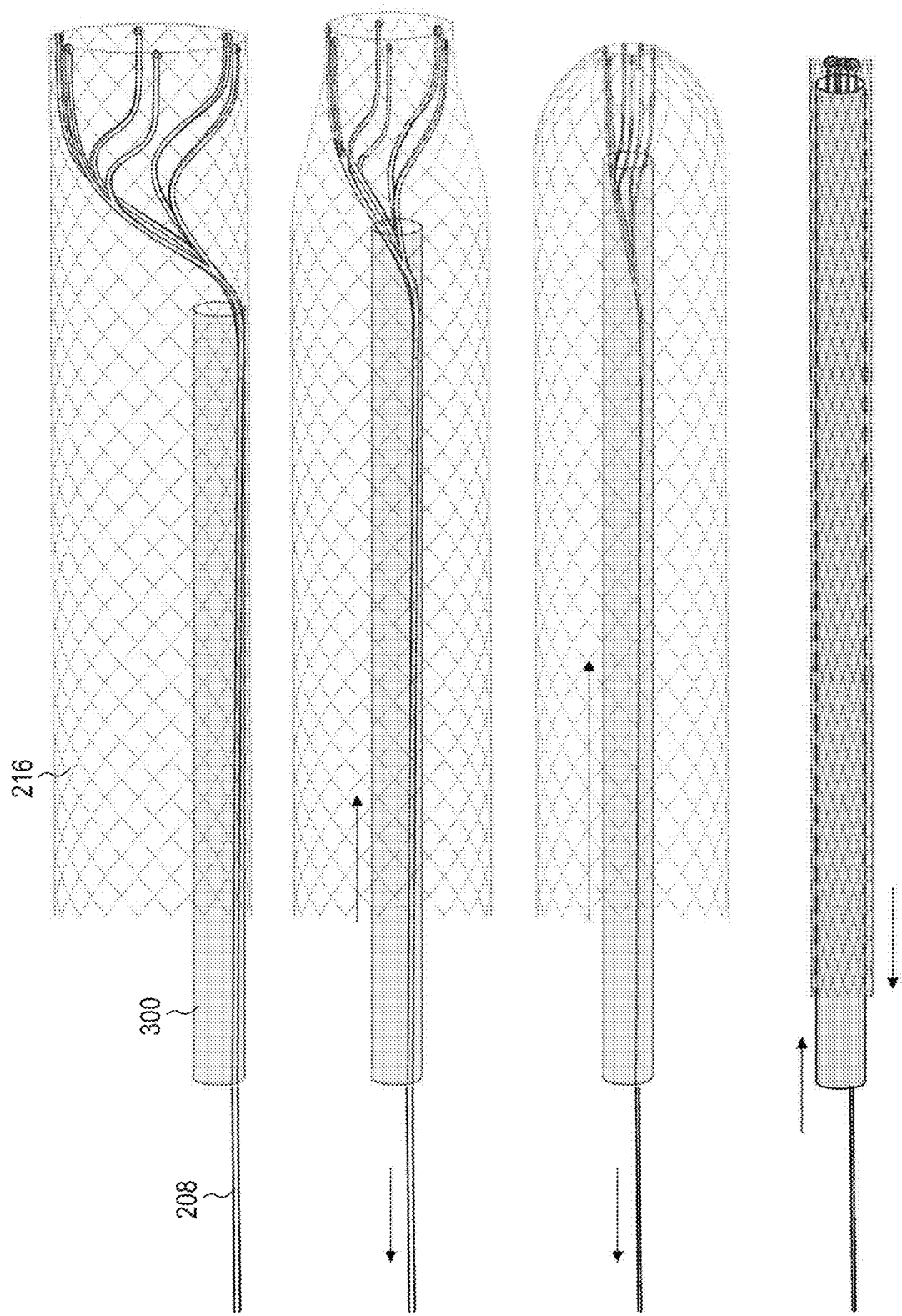
FIG. 4 shows exemplary steps for self-collapsing a braided section of an exemplary elongated tube using the actuator tube and actuation wire system.

FIG. 4 shows the steps of FIG. 3 in an exemplary embodiment where the collapsible section of the elongated tube is braided. Actuator tube 300 and actuation wire 208 may maintain elongated tube 200 in the collapsed state during delivery and, as illustrated in FIG. 4, also cause elongated tube 200 to transition from the expanded state to the collapsed state, for example, after removal of the obstruction from the blood vessel such that the catheter is removable from a subject in the collapsed state. As actuator tube 300 (e.g., a microcatheter) is advanced relative to the nitinol wire, this causes the self-collapse mechanism (e.g., the distal region of actuation wire 208) to be drawn into the microcatheter lumen. This causes the distal multi-armed structure to collapse radially inwards. When the self-collapse mechanism is fully withdrawn into microcatheter lumen, the distal tip of the braid is fully collapsed and the microcatheter is effectively attached to the distal end of the braid. By advancing the microcatheter even further, the braid is elongated and the entire braided structure can be collapsed onto the microcatheter, as shown at the bottom of FIG. 4.

Methods of using catheter 100 are also provided herein. As should be understood, descriptions of the methods are for illustration only, the order of steps may be modified, and the steps are optional unless explicitly stated as mandatory.

Figure 5A:
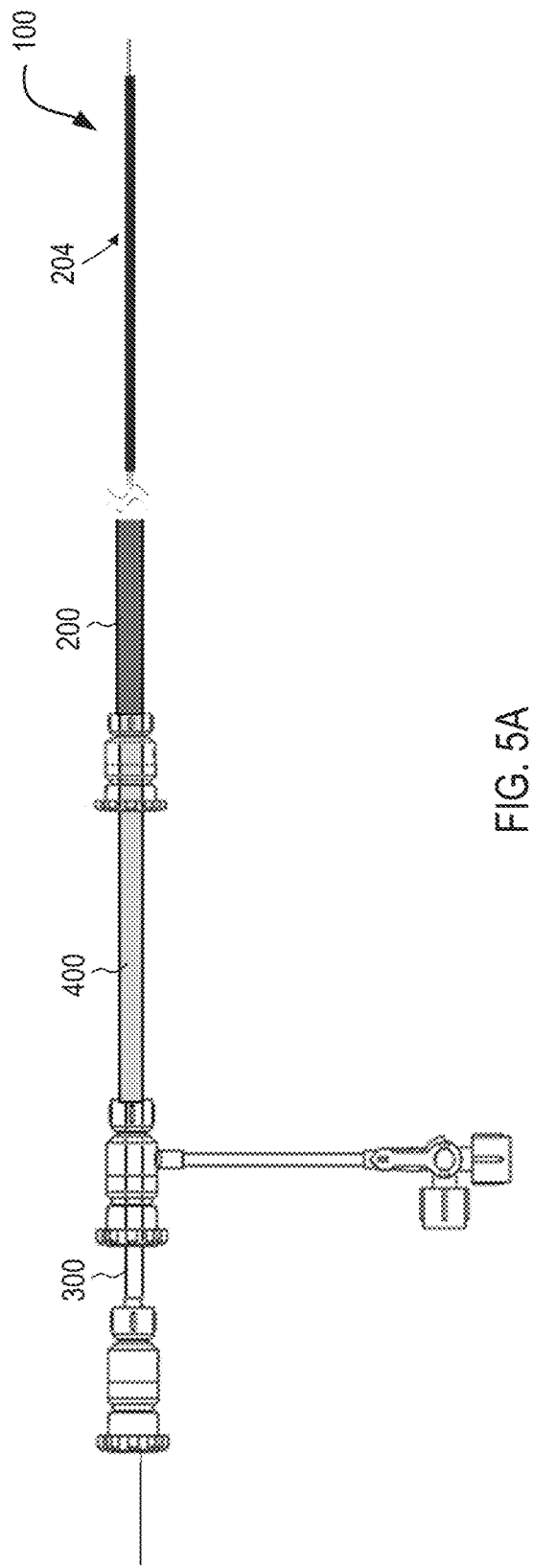

FIGS. 5A through 5H show an exemplary method for transitioning catheter 100 between the collapsed state and the expanded state. For illustrative purposes, the collapsible and expandable distal region of elongated tube will be described as a braided section. Referring to FIG. 5A, catheter 100 is shown in the collapsed state for delivery. As shown, actuator tube 300 is disposed within the lumen of elongated tube 200 and the distal region of actuation wire 208 is collapsed within actuator tube 300. As such, actuator tube 300 is fully extended and locked (e.g., via one or more hemostasis valves) with the elongated/collapsed distal braid ready for delivery. Further, actuator tube 300 may be disposed within the lumen of intermediate tube 400, which is disposed within the lumen of elongated tube 200. However, the distal end of intermediate tube 400 is positioned proximally to the distal end of elongated tube 200 such that the braided section of elongated tube 200 is collapsed on actuator tube 300. For example, the distal end of intermediate tube 400 may be positioned proximal to the braided section of elongated tube 200 in the delivery state.

Figure 5B:
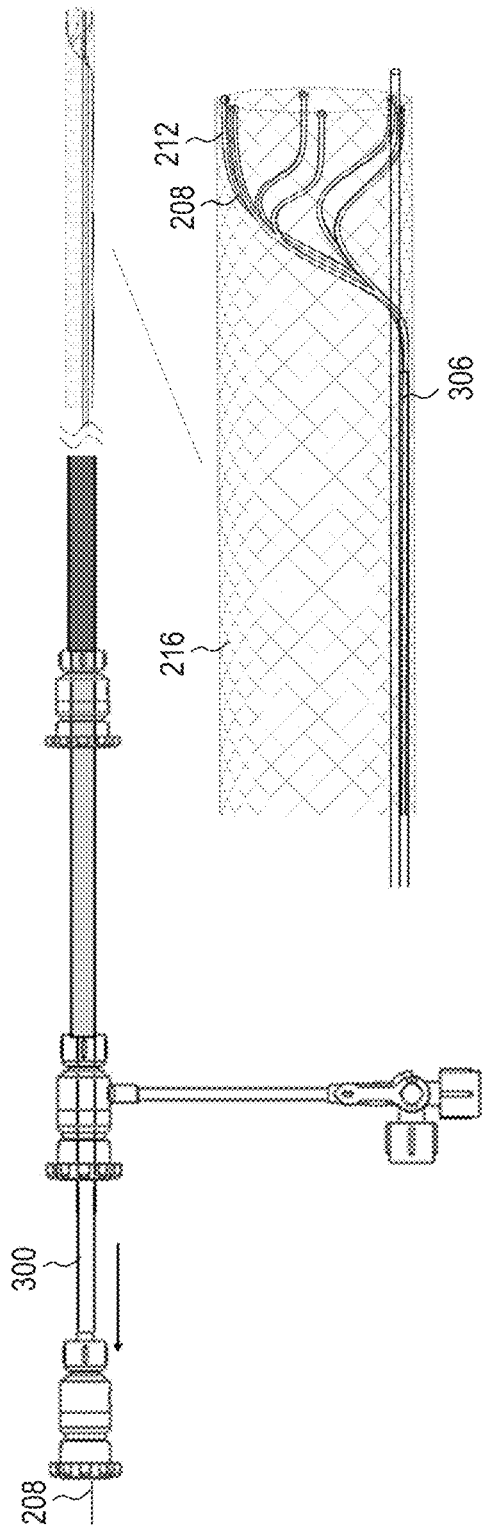

FIG. 5B shows elongated tube 200 transitioned from the collapsed state to the expanded state. For example, actuator tube 300 may be unlocked (via one or more hemostasis valves) such that the force applied to elongate the distal braid is removed thus causing braid 216 to expand. Braid 216 may expand when struts 212 of actuation wire 208 are exposed out the distal end of lumen 306 of actuator tube 300, causing struts 212 to self-expand thereby self-expanding braid 216.

Figure 5C:
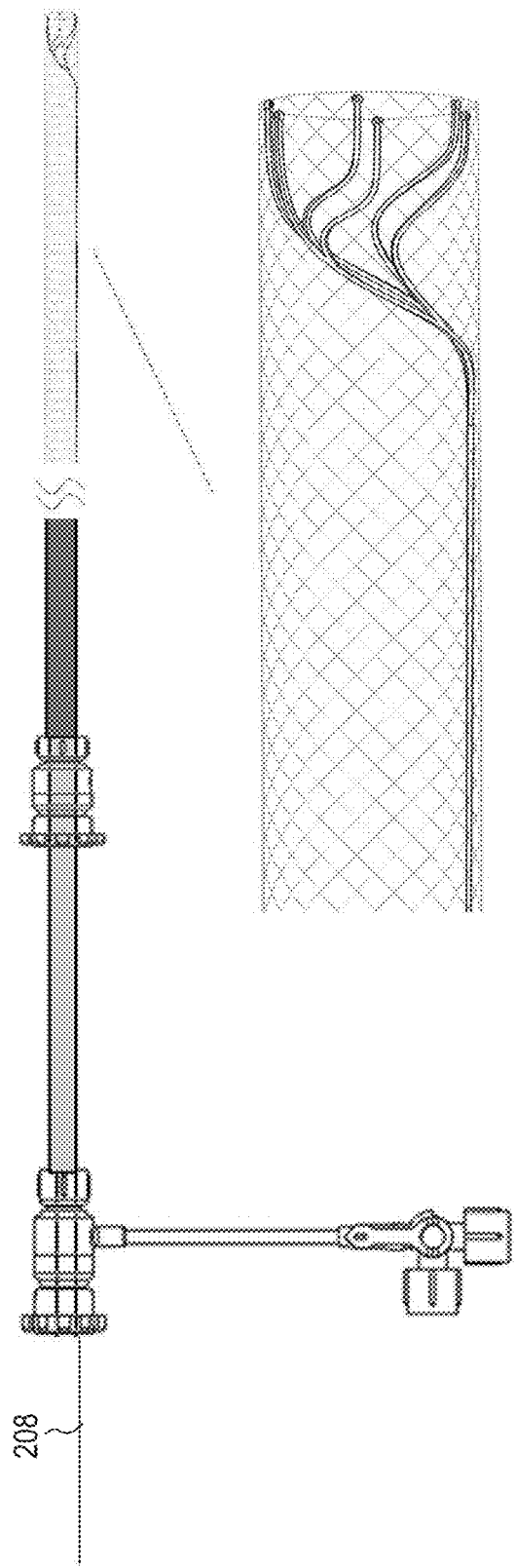

Referring now to FIG. 5C, actuator tube 300 is fully removed, for example, by translating actuator tube 300 proximally along actuation wire 208.

Figure 5D:
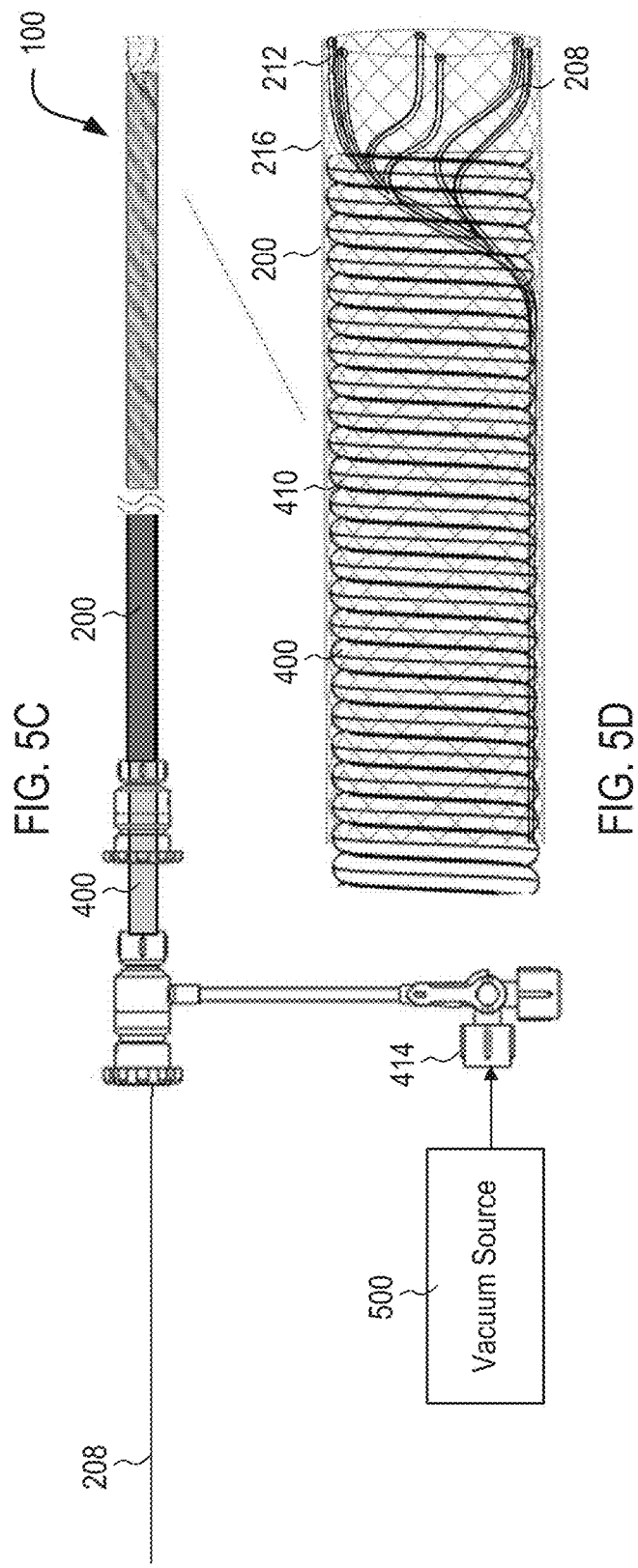

In FIG. 5D, intermediate tube 400 is translated relative to elongated tube 200. For example, intermediate tube 400 may be advanced distally to push coil 410 into the lumen of the collapsible/expandable section of elongated tube 200 (e.g., the braid lumen) while elongated tube 200 is in the expanded state. Intermediate tube 400 may be advanced distally to contact struts 212, as shown. As such, struts 212 may stop distal advancement of intermediate tube 400 so that the distal end of intermediate tube does not extend to or past the distal end of elongated tube 200. Intermediate tube 400 preferably reinforces the braid, for example, to permit aspiration to suck an obstruction into catheter 100. For example, vacuum source 500 may be coupled to catheter 100 to apply suction within elongated tube 200 to suck the obstruction into elongated tube 200 while in the expanded state to remove the obstruction from a blood vessel. Vacuum source 500 is a device capable of applying suction within a catheter tube for removing obstruction(s). In some embodiments, vacuum source 500 is coupled to intermediate tube 400 (e.g., via one or more valves 414) to apply suction within the lumen of intermediate tube 400. Thus, the obstruction may be sucked into the lumen of intermediate tube 400 while intermediate tube 400 is within the lumen of elongated tube 200.

Figure 5E:
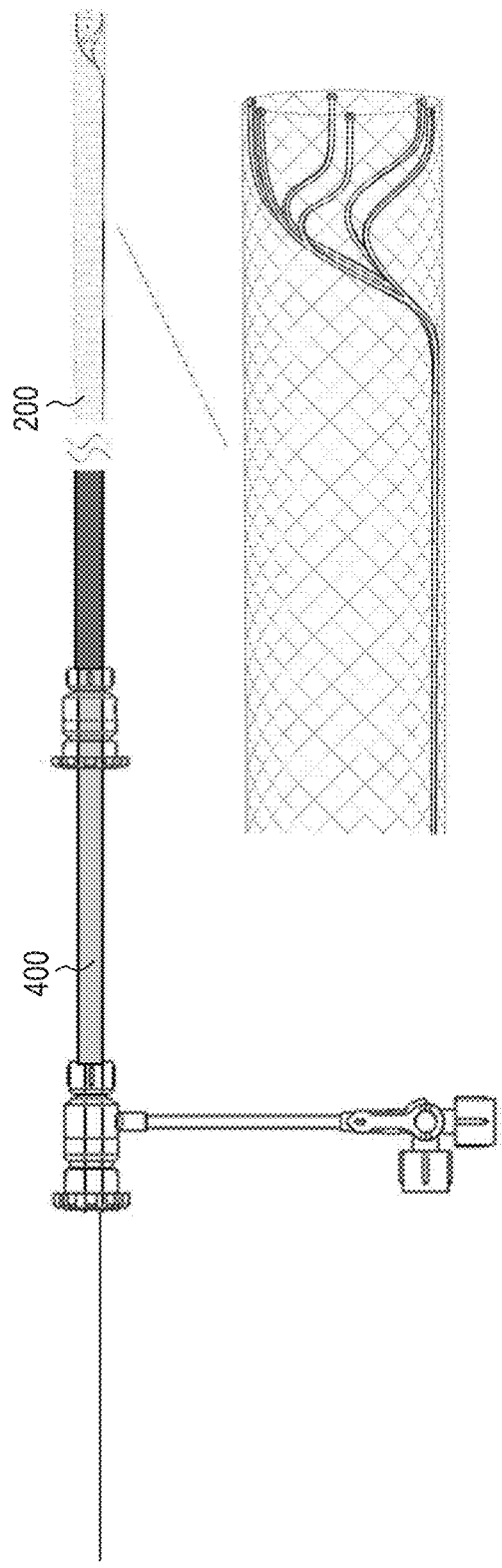

Referring now to FIG. 5E, intermediate tube 400 is retracted proximally relative to the distal end of elongated tube 200. For example, intermediate tube 400 may be moved proximally to remove intermediate tube 400 from the lumen of the collapsible/expandable portion of elongated tube 200 (e.g., from the braid lumen).

Figure 5F:
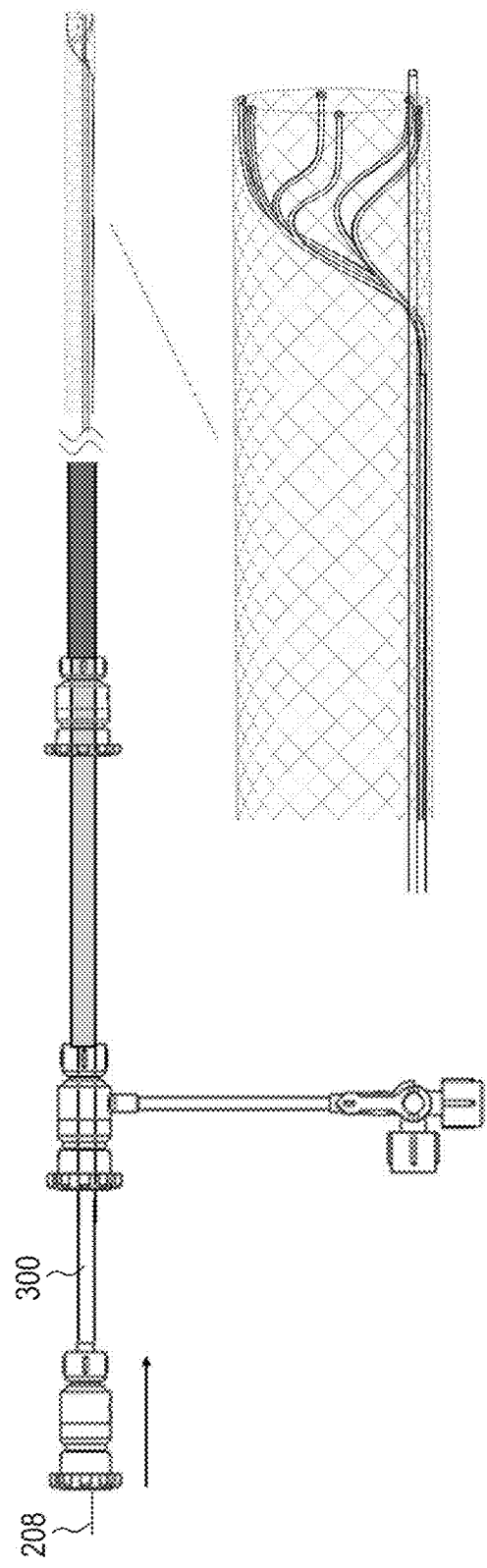

As shown in FIG. 5F, actuator tube 300 is reinstalled over actuation wire 208. For example, actuator tube 300 advanced distally within the lumen of elongated tube 200 (and within the lumen of intermediate tube 400). Actuator tube 300 may be advanced to the articulated region of actuation wire 208.

Referring now to FIG. 5G, actuator tube 300 is advanced relative to elongated tube 200 (and intermediate tube 400) to recapture distal collapse mechanism and narrow the distal braid lumen. For example, actuator tube 300 may be advanced distally relative to actuation wire 208 until struts 212 of actuation wire 208 collapse thereby causing the distal end of braid 216 to collapsed.

In FIG. 5H, actuator tube 300 is advanced fully to cause the collapsible section of elongated tube 200 to fully collapse. For example, the struts of actuation wire 208 may be fully collapsed within the lumen of actuator tube 300 and actuator tube 300 advanced distally to cause the braid diameter to be reduced and the braid length to be lengthened into the collapsed state. Actuator tube 300 may be locked (e.g., via one or more hemostasis valves) in the fully advanced position. Catheter 100 may then be removed from the patient in the collapsed state. Alternatively, catheter 100 could then be moved to a different position in the blood vessel (or another blood vessel) to remove one or more addition obstructions using the methods described herein.

FIGS. 6A through 6F show an exemplary method for removing an obstruction from a blood vessel using catheter 100. An obstruction within a blood vessel is identified using standard visualization techniques. For example, a patient experiencing ischemic stroke may be determined to have an obstruction O in the M1 segment of the middle cerebral artery MCA branching from the internal carotid artery ICA.

Figure 6B:
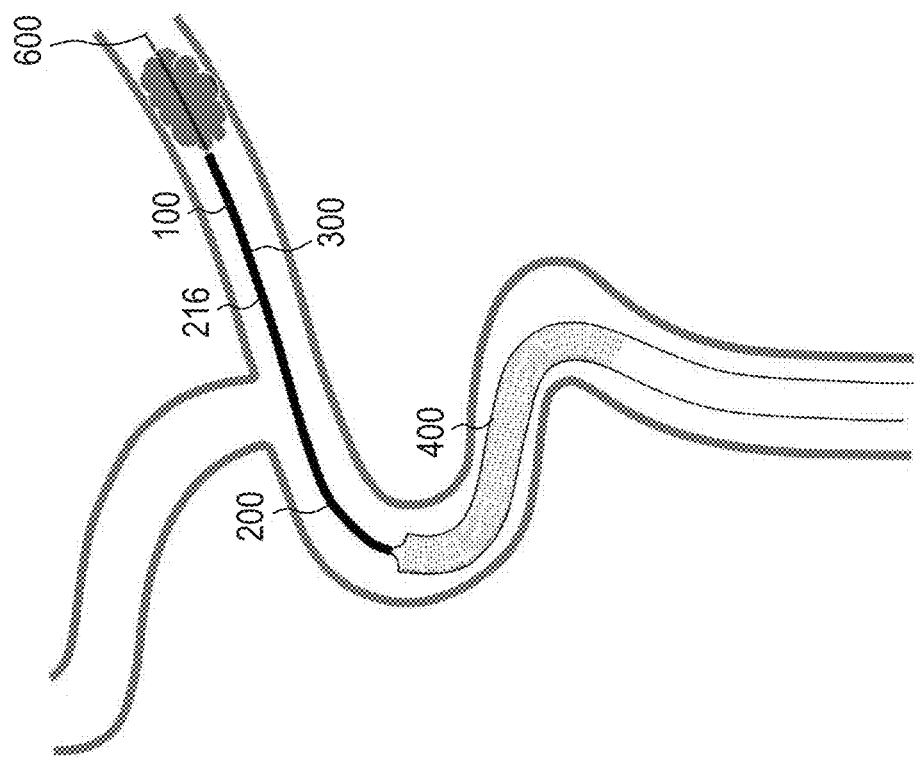
FIGS. 6A through 6F show an exemplary method for removing an obstruction from a blood vessel using a catheter described herein.
Figure 6A:
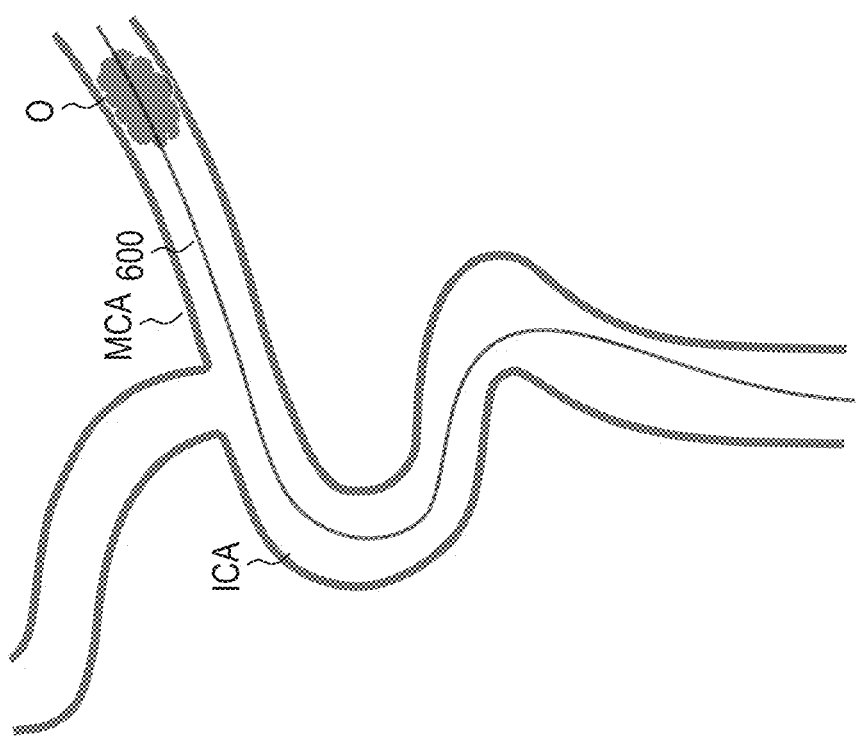

As shown in FIG. 6A, a clinician may navigate guidewire 600 to target obstruction O. The distal end of guidewire 600 may cross the obstruction O as illustrated. Next, as shown in FIG. 6B, catheter 100 may be advanced over guidewire 600 until the distal tip of catheter 100 is positioned within at a desired location within the blood vessel, such as just proximal to the obstruction O. In some embodiments, guidewire 600 is advanced through the guidewire lumen in actuator tube 300 of catheter 100.

Figure 6D:
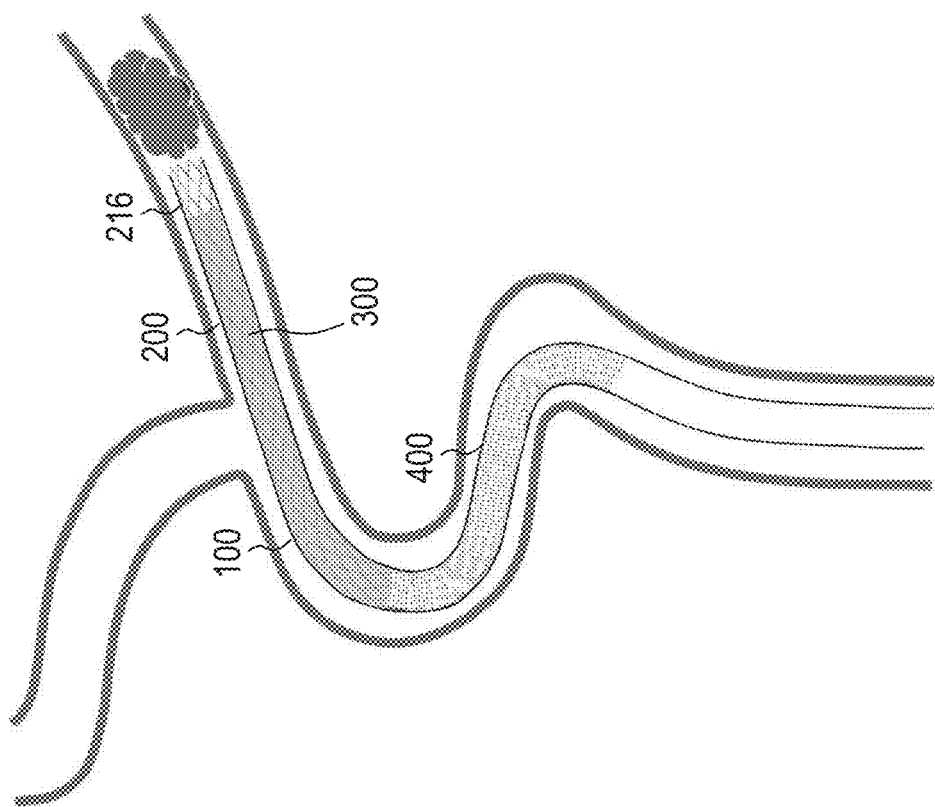
Figure 6C:
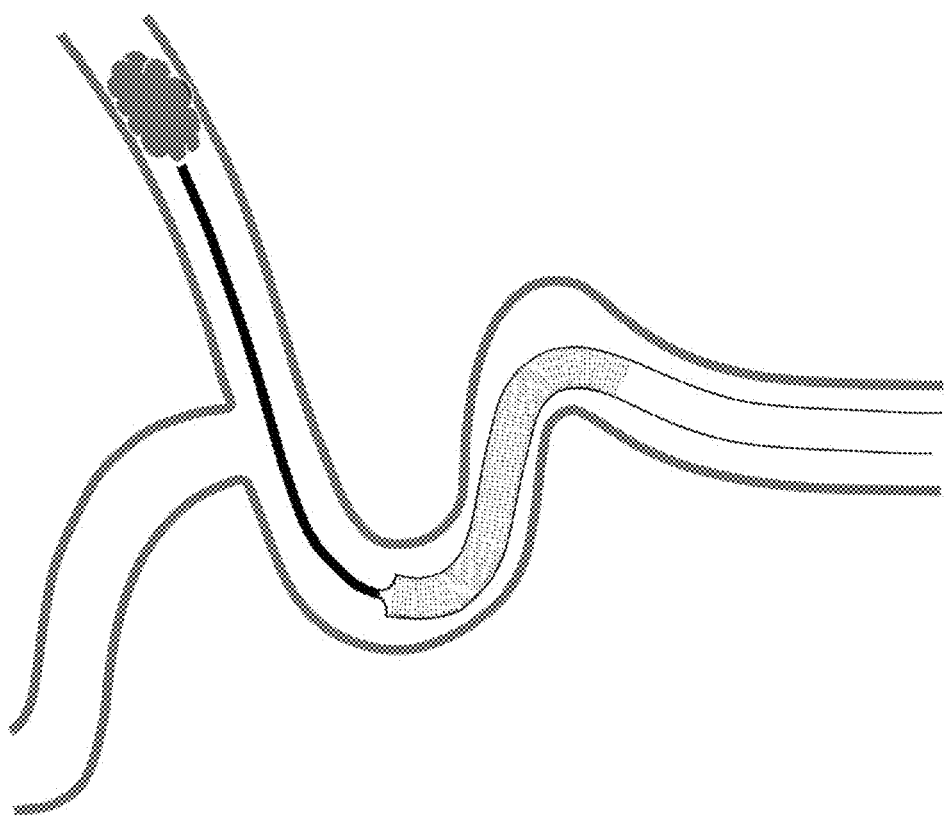

Then, the guidewire may be removed from catheter 100, and thereby from the patient, as shown in FIG. 6C.

Then, as shown in FIG. 6D, while the clinician holds the distal tip of catheter 100 in place (e.g., by holding the proximal end of the actuation wire), actuator tube 300 is unlocked (e.g., by unlocking a hemostasis valve) to expand distal braid 216 of elongated tube 200. For example, actuator tube 300 may be translated relative to actuation wire 208 to cause a plurality of struts of actuation wire 208 to expand radially outward to transition elongated tube 200 to an expanded state within the blood vessel. In some embodiments, actuator tube 300 may be moved proximally relative to the actuation wire such that the expandable distal portion of the actuation wire is exposed from the lumen of actuator tube and expands, thereby causing the braid to expand. The actuator tube may then be removed from the patient.

Figure 6E:
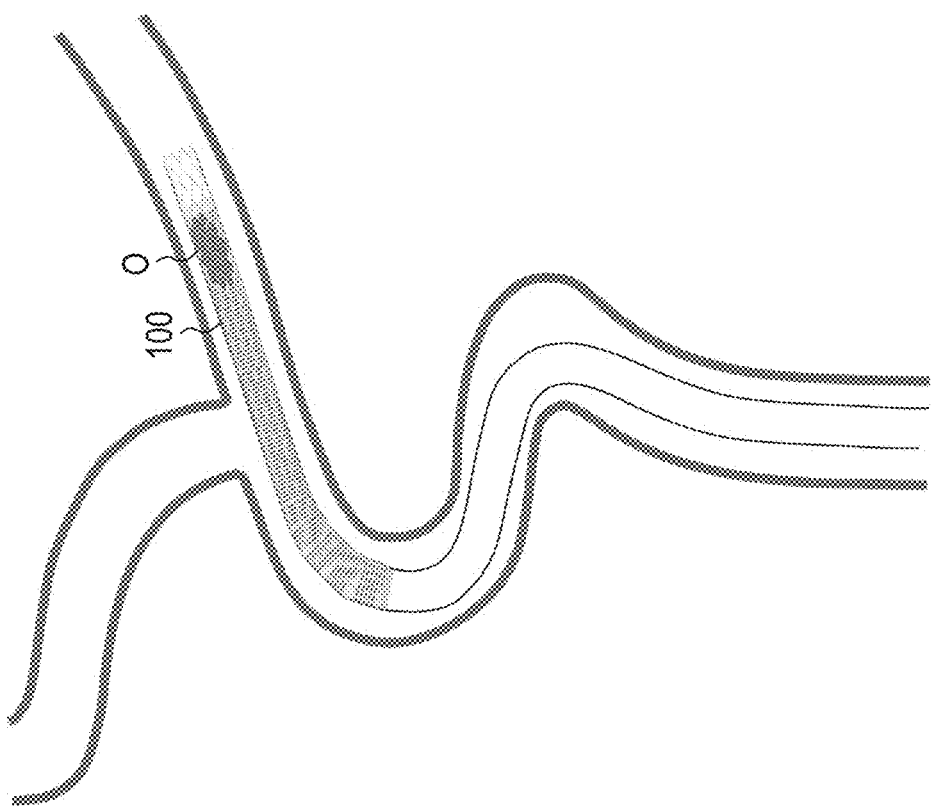
Figure 6F:
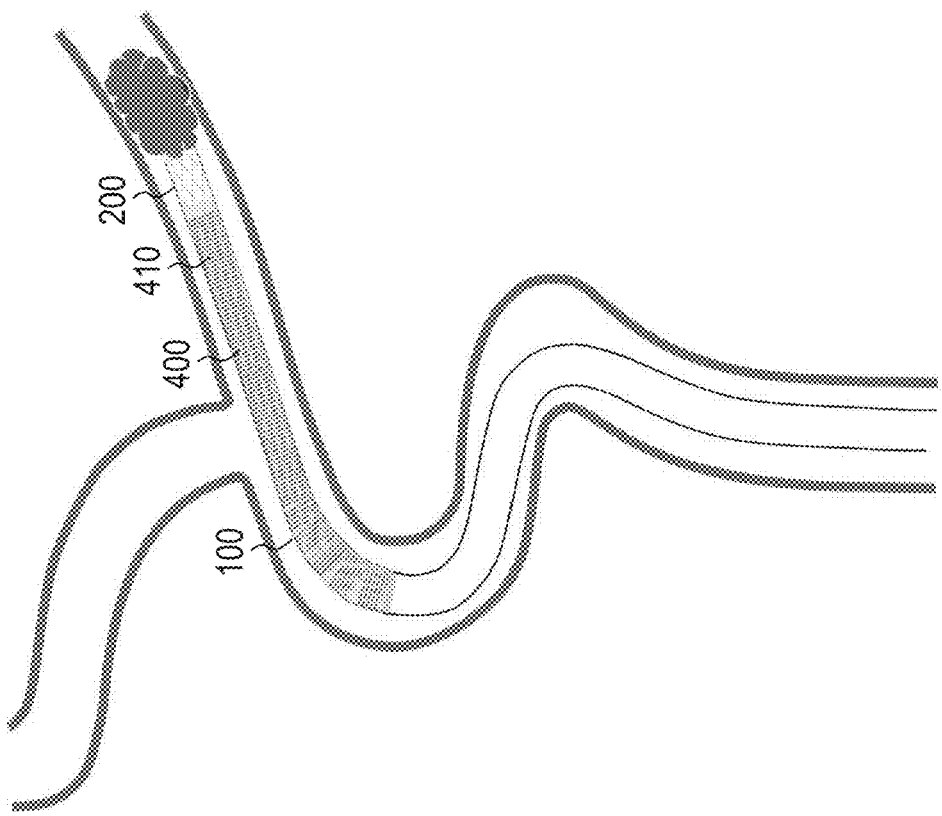
Figure 7A:
FIGS. 7A through 7F show side views of the exemplary method of FIGS. 6A through 6F.
Figure 7B:
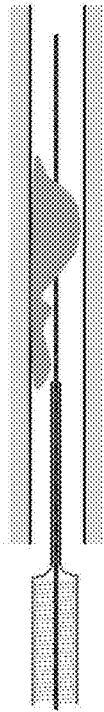
Figure 7C:
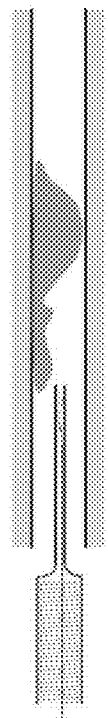
Figure 7D:
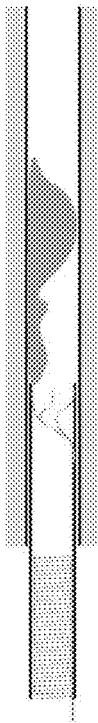
Figure 7E:
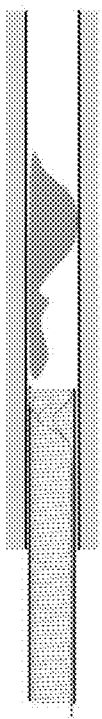
Figure 7F:
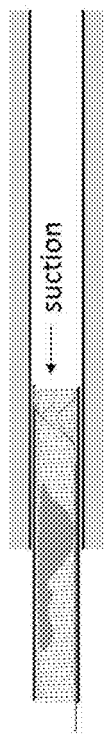

Referring now to FIG. 6E, intermediate tube 400 is advanced distally relative to elongated tube 200 such that the coiled portion of intermediate tube is disposed in the braid lumen to reinforce the distal catheter shaft. Next, suction may be applied into the lumen of the catheter such that the obstruction is aspirated into the lumen of catheter 100, as shown in FIG. 6F. Next, the catheter may be transitioned from the expanded state to the collapsed state, as described above with respect to FIGS. 5E through 5H such that the catheter is removed from the patient or moved elsewhere in the collapsed state. For example, actuator tube 300 may be translated relative to actuation wire 208 to cause the plurality of struts of actuation wire 208 to collapse radially inward to transition elongated tube 200 to the collapsed state within the blood vessel for repositioning/removal.

FIGS. 7A through 7F show side views of the exemplary method of FIGS. 6A through 6F for further clarity.

While various illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed:

1. A catheter for navigation to a target site in a blood vessel, the catheter comprising:
   an elongated tube having a lumen and a distal braided portion, the distal braided portion configured to transition between an expanded state and a collapsed state, the distal braided portion sized and shaped to be navigated through the blood vessel to the target site in the blood vessel in the collapsed state;
   an actuator tube configured to be disposed within the elongated tube; and
   an actuation wire configured to be disposed within the actuator tube, the actuation wire comprising an elongated shaft and a plurality of struts extending therefrom via an articulation region, each one of the plurality of struts affixed about a circumference of the distal end of the distal braided portion,
   wherein translation of the actuator tube relative to the actuation wire causes the plurality of struts to expand radially outward to transition the distal braided portion to the expanded state at the target site in the blood vessel.

2. The catheter of claim 1, further comprising an expandable biocompatible coating at the distal braided portion.

3. The catheter of claim 1, wherein the distal braided portion is collapsible via longitudinal force at the distal end of the distal braided portion such that the distal braided portion is longer in the collapsed state than in the expanded state.

4. The catheter of claim 1, further comprising an intermediate tube configured to be positioned between the elongated tube and the actuator tube, wherein a distal portion of the intermediate tube is configured to be advanced distally into the distal braided portion to reinforce the distal braided portion.

5. The catheter of claim 4, wherein the distal portion of the intermediate tube comprises a metal coil having a biocompatible coating.

6. The catheter of claim 5, wherein the metal coil is formed from nitinol and the biocompatible coating is PTFE.

7. The catheter of claim 1, further comprising a vacuum source configured to apply suction within the elongated tube to suck an obstruction at the target site in the blood vessel into the distal braided portion while in the expanded state to remove the obstruction from the blood vessel.

8. The catheter of claim 1, wherein the actuator tube and the actuation wire are configured to maintain the distal braided portion in the collapsed state during delivery and also cause the distal braided portion to transition from the expanded state to the collapsed state such that the catheter system is removable from a subject in the collapsed state.

9. The catheter of claim 1, wherein each strut of the plurality of struts has a curvature to facilitate even collapse of the actuation wire.

10. The catheter of claim 9, wherein the curvature ensures that a distance from a distal tip of each strut to an apex of the actuation wire proximal to the plurality of struts is the same.

11. The catheter of claim 1, wherein the articulation region comprises a branched structure.

12. The catheter of claim 1, wherein each strut of the plurality of struts comprises an eyelet at a distal tip for coupling to the distal braided portion.

13. The catheter of claim 1, wherein the elongated wire is offset from a central longitudinal axis of the elongated tube in the expanded state.

14. The catheter of claim 1, wherein distal ends of the plurality of struts are spaced apart equidistant about the circumference of the distal end of the distal braided portion.

15. The catheter of claim 1, wherein the actuation wire is formed of nitinol.

16. The catheter of claim 15, wherein the plurality of struts are laser cut from a nitinol tube.

17. The catheter of claim 16, wherein the plurality of struts are coupled to the elongated shaft via welding at the articulation region.

18. The catheter of claim 1, wherein the elongated tube is configured to permit insertion of one or more interventional devices into the lumen while the distal braided portion is in the expanded state at the target site in the blood vessel.

19. The catheter of claim 1, wherein the plurality of struts are configured to self-expand radially outward to the expanded state when exposed from an actuation lumen of the actuator tube.

20. The catheter of claim 1, wherein the actuator tube comprises a dual lumen microcatheter having a guidewire lumen configured to receive a guidewire.

21. The catheter of claim 20, wherein the guidewire lumen extends more distally than an actuation lumen for the actuation wire in the actuator tube.

22. The catheter of claim 1, wherein the distal end of the catheter is sized and shaped to be navigated to the target site in the blood vessel within a brain.

23. The catheter of claim 22, wherein the distal end of the catheter is sized and shaped to be navigated to a middle cerebral artery within the brain for removal of an obstruction therein to treat stroke.

24. The catheter of claim 1, wherein the elongated tube comprises a proximal region formed of a different material than the distal braided portion.

25. The catheter of claim 24, wherein the proximal region is formed from polymer and has a fixed diameter such that only the distal braided portion of the elongated tube has a variable diameter.

26. A method for navigating to a target site in a blood vessel using a catheter, the method comprising:

navigating a distal braided portion of an elongated tube in a collapsed state through the blood vessel to the target site while an actuator tube is disposed within the elongated tube;

translating the actuator tube relative to an actuation wire to cause a plurality of struts of the actuation wire to expand radially outward to transition the distal braided portion to an expanded state within the blood vessel, wherein each one of the plurality of struts is affixed about a circumference of the distal end of the distal braided portion; and performing an intervention at the target site in the blood vessel using the elongated tube while the distal braided portion is in the expanded state.

27. The method of claim 26, wherein performing the intervention comprises removing an obstruction from the blood vessel at the target site.

28. The method of claim 27, wherein removing the obstruction from the blood vessel comprises aspirating the obstruction using the catheter.

29. The method of claim 26, wherein performing the intervention comprises inserting one or more interventional devices into a lumen of the elongated tube while the distal braided portion is in the expanded state at the target site in the blood vessel.

30. The method of claim 26, wherein navigating the distal braided portion comprises navigating the distal braided portion of the elongated tube in the collapsed state through the blood vessel to the target site in a brain.

* * * * *